(12) United States Patent
Werblin

(10) Patent No.: US 7,811,320 B2
(45) Date of Patent: *Oct. 12, 2010

(54) INTRAOCULAR LENS SYSTEM

(75) Inventor: Theodore P. Werblin, Bluefield, WV (US)

(73) Assignee: Werblin Research & Development Corp., Princeton, WV (US)

(*) Notice: Subject to any disclaimer, the term of this patent is extended or adjusted under 35 U.S.C. 154(b) by 86 days.

This patent is subject to a terminal disclaimer.

(21) Appl. No.: 12/000,364

(22) Filed: Dec. 12, 2007

(65) Prior Publication Data

US 2008/0215147 A1    Sep. 4, 2008

Related U.S. Application Data

(63) Continuation-in-part of application No. 11/698,875, filed on Jan. 29, 2007.

(51) Int. Cl.
   *A61F 2/16* (2006.01)
(52) U.S. Cl. .................................. 623/6.34; 623/6.32
(58) Field of Classification Search ............... 623/6.32, 623/6.34, 6.22, 6.4–6.41, 6.43–6.44, 6.46–6.47
   See application file for complete search history.

(56) References Cited

U.S. PATENT DOCUMENTS

| 2,036,379 A | 4/1936 | Woodward |
| 2,039,144 A | 4/1936 | Burgess |
| 2,168,925 A | 8/1939 | Hewes |
| 2,354,586 A | 7/1944 | Fischer |
| 2,798,373 A | 7/1957 | Harza |
| 2,806,809 A | 9/1957 | Schuh |
| 3,128,576 A | 4/1964 | Bradley |
| 3,194,130 A | 7/1965 | Guntert |
| 3,200,482 A | 8/1965 | Brown |
| 3,265,556 A | 8/1966 | Hungerford |

(Continued)

FOREIGN PATENT DOCUMENTS

DE    707212    5/1941

(Continued)

OTHER PUBLICATIONS

Werblin et al., "Epikeratophakia: The surgical correction of aphakia. III. Preliminary results of a prospective clinical trial," 93 Arch. Opth., pp. 342-347 (1982).

(Continued)

*Primary Examiner*—Corrine M McDermott
*Assistant Examiner*—Tiffany Shipmon
(74) *Attorney, Agent, or Firm*—Arent Fox LLP

(57) ABSTRACT

A multi-component intraocular lens implanted in an optical system of a human eye, including one or more foldable removable components, each component being foldable. One component acts as a base lens, including a flange with a slot. Another component acts an optical assembly that may include a top lens joined to or integrated with a mid lens. The top lens, the mid lens or the optical assembly may include at least one projection that engages the slot of the base lens. A medical adhesive may be applied to an outer circumferential surface of the top lens to join the top lens to the mid lens or may be applied to a top surface of the top lens opposing a bottom surface of the mid lens.

26 Claims, 22 Drawing Sheets

U.S. PATENT DOCUMENTS

| | | | |
|---|---|---|---|
| 3,269,282 A | | 8/1966 | Beesley et al. |
| 3,458,870 A | | 8/1969 | Stone, Jr. |
| 3,945,054 A | | 3/1976 | Fedorov et al. |
| 4,010,496 A | | 3/1977 | Neefe |
| 4,240,163 A | | 12/1980 | Galin |
| 4,373,218 A | | 2/1983 | Schachar |
| 4,402,579 A | | 9/1983 | Poler |
| 4,575,373 A | | 3/1986 | Johnson |
| 4,585,456 A | | 4/1986 | Blackmore |
| 4,585,457 A | | 4/1986 | Kalb |
| 4,636,212 A | | 1/1987 | Posin et al. |
| 4,655,770 A | | 4/1987 | Gupta et al. |
| 4,685,921 A | | 8/1987 | Peyman |
| 4,685,922 A | | 8/1987 | Peyman |
| 4,731,078 A | | 3/1988 | Stoy et al. |
| 4,769,035 A | | 9/1988 | Kelman |
| 4,778,463 A | | 10/1988 | Hetland |
| 4,787,903 A | | 11/1988 | Grendahl |
| 4,834,754 A | | 5/1989 | Shearing |
| 4,838,266 A | | 6/1989 | Koziol et al. |
| 4,842,601 A | | 6/1989 | Smith |
| 4,863,466 A | | 9/1989 | Schlegel |
| 4,892,543 A | | 1/1990 | Turley |
| 4,932,971 A | | 6/1990 | Kelman |
| 4,950,289 A | | 8/1990 | Krasner |
| 5,066,301 A | | 11/1991 | Wiley |
| 5,085,013 A | * | 2/1992 | Ascosi et al. ............... 451/460 |
| 5,098,444 A | | 3/1992 | Feaster |
| 5,133,748 A | * | 7/1992 | Feaster ...................... 623/6.12 |
| 5,171,267 A | | 12/1992 | Ratner et al. |
| 5,196,027 A | | 3/1993 | Thompson et al. |
| 5,222,981 A | | 6/1993 | Werblin |
| 5,288,293 A | | 2/1994 | O'Donnell, Jr. |
| 5,366,502 A | | 11/1994 | Patel |
| 5,628,798 A | * | 5/1997 | Eggleston et al. .......... 623/6.11 |
| 5,728,155 A | | 3/1998 | Anello et al. |
| 5,777,719 A | | 7/1998 | Williams et al. |
| 5,892,617 A | | 4/1999 | Wallace |
| 5,943,117 A | | 8/1999 | Van de Velde |
| 5,968,094 A | * | 10/1999 | Werblin et al. ............. 623/6.34 |
| 6,113,633 A | * | 9/2000 | Portney ..................... 623/6.32 |
| 6,254,637 B1 | * | 7/2001 | Lee et al. ................... 623/5.14 |
| 6,255,338 B1 | | 7/2001 | Duncan et al. |
| 6,413,276 B1 | | 7/2002 | Werblin |
| 6,524,340 B2 | | 2/2003 | Israel |
| 6,551,354 B1 | | 4/2003 | Ghazizadeh et al. |
| 6,991,651 B2 | * | 1/2006 | Portney ..................... 623/6.34 |
| 7,008,449 B2 | | 3/2006 | Willis et al. |
| 7,097,660 B2 | * | 7/2006 | Portney |
| 7,300,464 B2 | * | 11/2007 | Tran .......................... 623/6.41 |
| 2002/0161436 A1 | * | 10/2002 | Portney ..................... 623/6.34 |
| 2003/0204254 A1 | | 10/2003 | Peng et al. |
| 2005/0125058 A1 | | 6/2005 | Cumming et al. |
| 2006/0047339 A1 | * | 3/2006 | Brown ....................... 623/6.13 |

FOREIGN PATENT DOCUMENTS

| | | |
|---|---|---|
| DE | 3 428 895 A1 | 2/1986 |
| DE | 3428895 | 2/1986 |
| EP | 0 269 197 A1 | 6/1988 |
| EP | 0 269 198 A1 | 6/1988 |
| EP | 0 435 528 B1 | 7/1991 |
| EP | 0 435 525 B1 | 3/1995 |
| FR | 2666735 | 3/1992 |
| WO | WO 91/06259 A1 | 5/1991 |
| WO | WO 9220302 | 11/1992 |

OTHER PUBLICATIONS

Werblin et al., "Hydrogel Keratophakia: Measurement of Intraocular Pressure," vol. 11, No. 4 CLAO Journal, pp. 354-357 (Oct. 1985).

Werblin et al., "Refractive Corneal Surgery: The Use of Implantable Alloplastic Lens Material," 11 Austrial Journal of Opthalmology, pp. 325-331 (1983).

Werblin "Lamellar Refractive Surgery: Where Have We Been and Where are we going?" vol. 5, No. 3, Refractive and Corneal Surgery, pp. 167-176 (Jan. 1989).

Binder et al. "Hydrogel Refractive Keratoplasty. Lens Removal and Exchanges" vol. 2, Cornea at pp. 119-125.

Werblin et al., Epikeratophakia: The surgical correction of aphakia. II. Preliminary results in a non-human primate model; 1(3) Curr. Eye Res., pp. 131-137; 1981.

Wikipedia, "Presbyopia", The Free Encyclopedia, pp. 1-4, Oct. 30, 2006.

Ernani Serpa Junior, et al., "Comparison of PMMA, foldable silicone and foldable acrylic hydrophobic intraocular lenses in combined phacoemulsification and trabeculectomy", Arq Bras Oftalmol. 2005; 68 (1):29-35.

Cyw Khng, et al., "The IOL flip: rescue for foldable lens implantation gone wrong", The BMJ Interview-BJO Online Journals, Oct. 30, 2006, pp. 1-5.

Cyw Khng, et al., "The IOL flip: rescue for foldable lens implantation gone wrong", BJO Online Journals, Br. J. Ophthalmol 2003;87;656-657 doi:10.1136/bjo.87.5.656.

Theodore P. Werblin, "Why Should Refractive Surgeons Be Looking Beyond the Corenea?", Barraquer Lecture 1998, Journal of Refractive Surgery vol. 15 May/Jun. 1999, pp. 359-376.

* cited by examiner

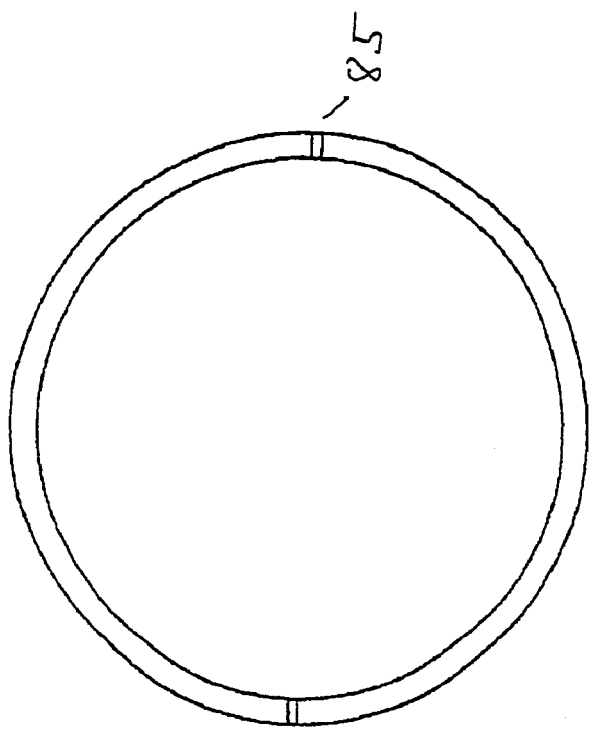
FIG.5A (RELATED ART)
FIG.5B (RELATED ART)

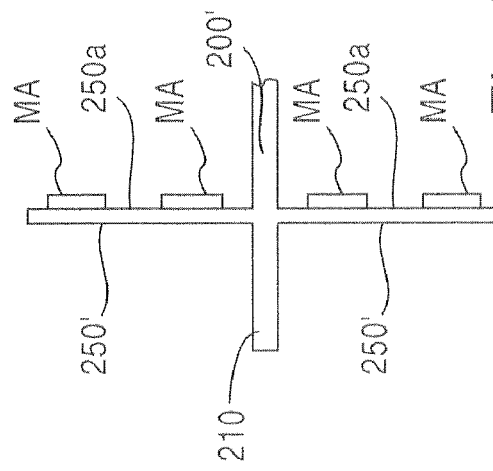
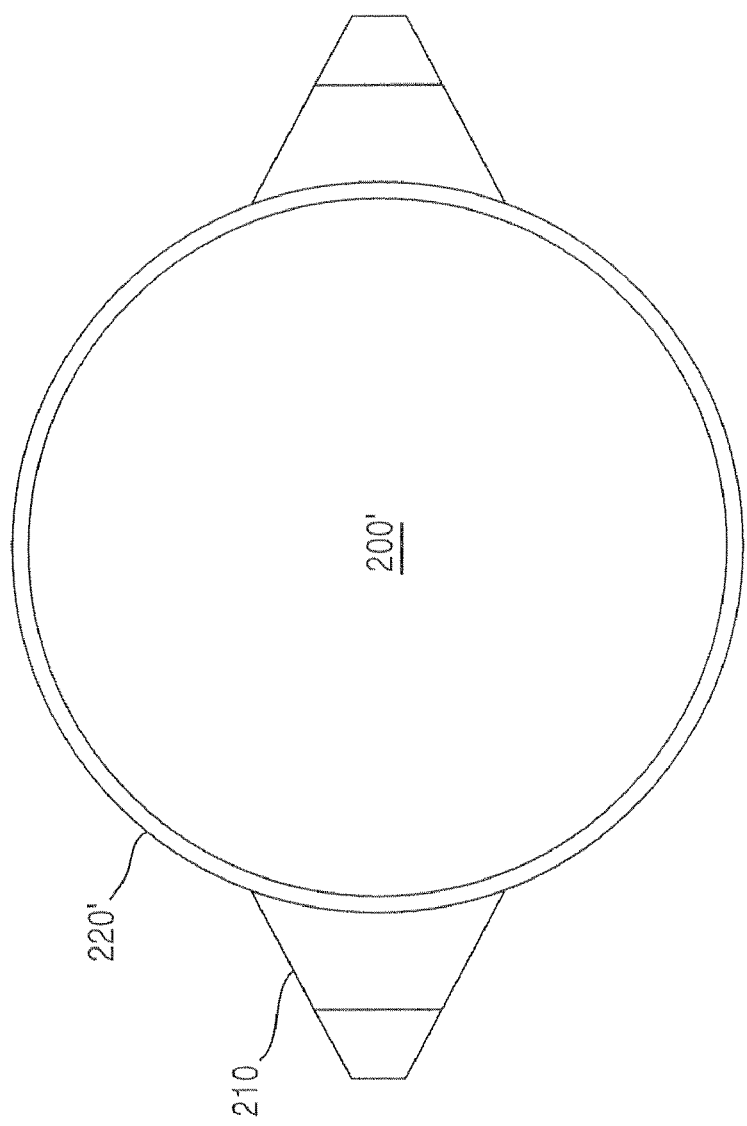

INTRAOCULAR LENS SYSTEM

CROSS-REFERENCE TO RELATED APPLICATION

This application is a continuation-in-part application of application Ser. No. 11/698,875 filed Jan. 29, 2007, the entire contents of which are incorporated herein by reference.

BACKGROUND OF THE INVENTION

1. Field of the Invention

This invention relates to a method for correcting the optical system of an eye using an intraocular lens system. Particularly, this invention relates to a method of correcting focusing abnormalities and optical aberrations measured by wave front or similar technology to quantify optical aberrations in the optical system of the eye, using a laser, or other apparatus and/or methods of fabricating or modifying a lens, for the optical system of an eye having a foldable, interchangeable intraocular lens system provided therein.

2. Description of Related Art

The field of refractive surgery has evolved rapidly during the past few decades. Current procedures and methods used by refractive surgeons may not satisfy the total refractive needs of the patient. Particularly, the most commonly performed refractive surgical procedures, such as, for example, cataract extraction with intraocular lens implantation, in addition to the most recently popularized corneal refractive surgical procedures, such as eximer laser photoblation, exhibit limitations. One reason for the limitations is the lack of post-operative refractive accuracy. The lack of post-operative refractive accuracy renders the commonly known refractive surgical procedures uncompetitive with currently available non-surgical alternatives for patients, for example, glasses and contact lenses. Further, because refractive surgery requires local or general anesthesia and incisions into the eye, a need exists for decreasing the trauma resultant from the surgery.

Recently, a need has arisen for efficient treatment of presbyopia, or the diminished power of accommodation of the eye. Presbyopia is a condition which typically affects a large number of people as they age, with the severity of the condition varying depending on the person. Difficulties arise in treating presbyopia because typically once a person manifests symptoms of presbyopia, the symptoms worsen as the person ages. As a person's condition worsens, a different, usually more powerful, lens is required to correct the condition. Conventional techniques for replacing an intraocular lens each time the patient's vision deteriorated do not always present a practical or cost-effective approach. Recent developments in the field, of refractive surgery have made intraocular treatment of presbyopia a feasible course of treatment for those patients that desire or need improved vision, however a need exists for more precise techniques and devices for use in refractive intraocular surgery.

Patients suffering from eye trauma or other eye afflictions may have the iris or other portions of the eye distorted, destroyed, or discolored. Currently, such patients are typically prescribed cosmetic contact lenses. Cosmetic intraocular lens replacement is emerging as a viable alternative, however a need exists for more efficient intraocular lens replacement in order to minimize eye trauma and establish cosmetic intraocular lens replacement as a safe and effective alternative to cosmetic contact lenses and other non-surgical treatments. As surgical techniques become more effective, safer, and less painful, patients may choose to have elective lens replacement surgery to change the color, structure, or shape of their eyes. By providing a minimally invasive method for lens replacement as described in an embodiment herein, the surgeon is able to limit the drawbacks of the procedure.

Current procedures and methods for refractive surgery require the performing surgeon to execute the procedure with a high level of skill and experience. Currently, methods and procedures for carrying out refractive surgery involving intraocular lenses generally require direct visualization of the intraocular lens assembly within the eye. Such visualization, although not outside the scope of a surgeon skilled in the art, increases the degree of difficulty of the procedure, thus increasing the chance that a surgical error or other problem will arise in the surgical procedure, leading to unwanted complications. Thus, a need exists for intraocular lens assemblies and systems whose structures provide less complex methods of insertion into and extraction from the eye.

Currently, refractive cataract surgeons performing the most common refractive surgical procedure, i.e., routine cataract surgery, obtain refractive accuracies in a +/−0.75 to +/−1.00 diopter (D) range. However, the industry has established goals of obtaining refractive accuracies in the +/−0.25 D range. Therefore, there is a need in the industry to provide a more accurate alternative to the current procedure. Furthermore, analyses of current corneal refractive technologies indicate the presence of a significant amount of preexisting or naturally occurring post-operative, as well as preoperative, image distortion (optical aberration) or degradation, particularly under low light conditions, such as when driving at night.

Due to the practical limits of performing intraocular surgery, as well as the biological and physical behavior of the human eye during and after various types of intraocular surgery, predictability at the +/−0.25 D accuracy level with a single surgical procedure is difficult to achieve as a practical matter. Furthermore, factors such as biometry errors, variable wound healing, and capsular contraction around the intraocular lenses contribute to decreasing the likelihood of achieving the desired refractive accuracy. Accordingly, practitioners in the industry have found that an adjustable intraocular lens (IOL), hereinafter referred to as the MC-IOL (multi-component) or C-IOL (compound), following lens extraction surgery provides a plurality of desirable options for refractive surgeons and patients.

An adjustable IOL allows fine tuning of the initial refractive result by exchanging at least one of the optical elements of the lens implant. As a result, accuracies in the +/−0.25 D range are readily attainable. Furthermore, patients are provided with an opportunity to exchange the "old" lens components with new and hopefully more accurate components. Such an objective is obtainable if the surgeon has an effective, efficient, and safe method of performing lens element exchanges. Additionally, months and/or years after the refractive surgical procedure, if the optical properties of the inserted IOL, for example, the multifocality, become problematic, the surgeon should have the ability to safely exchange the undesirable optical elements of the IOL to correct any optical aberrations that the patient will not or cannot tolerate.

In 1990, the inventor of this application developed a multi-component intraocular lens, hereinafter referred to as the MC-IOL (FIG. 1), for use following clear lens or refractive cataract surgery, wherein the optical properties of the MC-IOL can be modified at any post-operative time. The base intraocular lens component of the MC-IOL is shown in FIG. 1. The mid lens attaches to the top of the base lens and holds the third component of the MC-IOL, the top lens, in place.

The base intraocular lens 10 and the mid lens 20 each have securing flanges 16, 18 and 20, 24, respectively, extending therefrom. The MC-IOL also comprises at least one top lens 30, as illustrated in FIG. 1. The top lens 30 is positioned on top of the mid lens 20. See FIGS. 1-2.

The MC-IOL also includes projections (or haptics) 11 and 13 which securely hold the MC-IOL in the tissue of the human eye. The above-described structure permits the base intraocular lens 10 to form a platform upon which the mid lens 20 is placed, and to hold the top lens 30. During routine cataract surgery, the MC-IOL replaces the crystalline lens of the human eye. Once a patient's eye has healed after such a surgery, the surgeon reenters the eye and replaces, if necessary, and more than once, the top lens 30 and the mid lens 20 to modify the optical characteristics of the eye until the desired levels for each optical characteristic are attained.

FIGS. 3A-3B illustrate an assembled compound intraocular lens, hereinafter C-IOL, used with a preexisting lens within the human eye. The C-IOL has two components similar to the mid lens (FIGS. 4A-4B) and the top lens (FIGS. 5A-5B) components of the MC-IOL. FIG. 5A also illustrates the axis orientation mark 85 used in some embodiments of MC-IOL lenses, to aid in positioning and orienting the lens. The preexisting lens can be the crystalline lens of the eye with the C-IOL placed in the sulcus (FIG. 6) or in the anterior chamber angle (FIG. 7) of the eye's optical system. However, the C-IOL can also be used with a conventional IOL, as well as with an accommodating IOL, and mounted in the sulcus (FIG. 8), in the anterior chamber angle (FIG. 9), in the anterior chamber with posterior chamber fixation (FIG. 10) or in the anterior chamber with iris fixation (FIG. 11). Thus, a surgeon modifies the optical characteristics of the optical system of the eye by using the mid and top lenses in tandem with the preexisting conventional IOL implant or crystalline lens of the eye.

The C-IOL and MC-IOL provide numerous enhanced features. For example, the C-IOL and MC-IOL can each be structured as a monofocal or multifocal optical system, correct astigmatism, as well as comprise ultraviolet light-absorbing, tinted, or other such chemically treated materials.

It should be understood that there are various reasons why an adjustable MC-IOL or C-IOL is more desirable than a single component implant. In order to achieve all the permutations and combinations of the astigmatism, multifocality, and spherical correction needed to achieve emmetropia would take an inventory of over ten thousand lenses, whereas with the MC-IOL (multiple components) concept, an inventory of about one hundred components would be necessary. With anterior chamber lenses, progressive encapsulation or engulfment of the lens haptics by uveal tissue in the angle often occurs 1-2 years post-operatively. The engulfment typically makes the removal of the lenses and their haptics more difficult. Exchange of iris fixated anterior chamber lenses does not typically guarantee precise position or orientation. Posterior chamber lenses similarly cannot be removed because of posterior capsule fibrosis. Easy removal and exchangeability is critical for any customized emmetropic system, which can be provided by a specially designed multicomponent lens system.

Therefore, based on the above, a MC-IOL having three elements rather than one permits refractive customization and adjustability for all refractive errors, as well as for all patients, while using a minimal number of lens elements or parts and requiring little customization on the part of the manufacturer. Thus, it has become very important in the refractive surgery art to be able to individualize and/or customize surgery such that the surgeon can easily and safely, as well as accurately, modify the refractive power of an intraocular lens implant.

For example, U.S. Pat. No. 5,288,293 to O'Donnell, Jr. discloses a method of modifying a single IOL. O'Donnell suggests that the refractive power of a single IOL may be varied before implantation so that the changes can be made in situ by the ophthalmologist after determining the extent of correction required to improve the vision of the patient before the lens is made. However, the surgical implantation procedure itself may create additional optical aberrations which cannot be anticipated preoperatively and thus the primary lens implant cannot account for these optical aberrations.

As such, it may be argued that if a lens can be modified before being implanted, as suggested by O'Donnell, Jr., it should be possible to modify the implanted lens by removing the implanted lens, modifying the lens, and then reimplanting the modified lens into the optical system of the eye. However, the design of current intraocular lenses typically makes such a procedure difficult and impractical. Furthermore, after a period of time with normal healing, it becomes physically dangerous and/or nearly impossible to the patient to have the implanted lens removed once the eye tissue takes hold on the capsular fixation holes of the lens. Therefore, such an argument is not realistic, practical, or safe. A single component intraocular lens, which in general is not designed to be removed and with only two optical surfaces, cannot accurately allow for compensation of sphere, cylinder, cylindrical axis, and all forms of optical aberrations that may be discovered after the initial implantation. However, the MC-IOL typically will have four removable optical surfaces which can compensate for these optical properties.

The inventor of this application invented the previously discussed MC-IOL and C-IOL that are designed specifically to permit the easy exchange of optical elements at a post-operative period without risk to the human eye or to the patient, beyond the risk of ordinary intraocular surgery. The easy exchangeability of optical elements is critical because the actual surgery of implanting the lens in the first place, as well as variances in the manner in which the eye heals after implantation, potentially create distortions which may not stabilize for several months after the operation. Therefore, the ability to measure and to compensate for the distortion(s) optimally takes place several months after surgery and cannot typically be predicted prior thereto. Since the same surgical wound is used for both the primary and secondary operations, additional distortion due to wound healing would not be anticipated as a result of the second operation.

Furthermore, the ability to exchange optical elements of a multicomponent or compound intraocular lens can be economical compared to removing, modifying, and re-implanting a single component lens, as well as easier to perform.

The MC-IOL has four surfaces available for modification, two piano and two convex. Preferably, the modification is made only to the piano surfaces to avoid interfering with the convex side which may already be used for correction of astigmatism (cylinder) or used as a multifocal lens surface. The same preference applies to the CIOL, which has two surfaces available for modification, one piano and the other convex.

The inventor of this application also developed a system for correcting optical aberrations in the MC-IOL, as described, for example, in U.S. Pat. No. 6,413,276, for conducting measurements to determine any residual or new aberrations present in an operated eye after the biological healing parameters have stabilized, as well as to correct any errors in sphere, cylinder, or cylindrical axis, and for modifying one, two, or more existing lens elements within the implanted optical system based on the conducted measurements.

In conventional multi-component intraocular lens designs, the surgical procedure required to implant the intraocular lens components requires a high level of surgeon skill. For example, implantation of the removable component of the lens requires the surgeon to directly visualize the placement of the lens in order to match the notches with the flanges. Further, removal of the removable lens component requires a special forceps tool for grabbing the base lens, and releasing the tabs holding the sandwich and cap lens together with the base lens (see, for example, the system described in U.S. Pat. No. 5,968,094).

Historically intraocular lens systems used a rigid one piece poly methyl methacrylate (PMMA) lens. The PMMA lens is approximately six millimeters in diameter. Because the PMMA lens is rigid, insertion of the PMMA intraocular lens generally requires a seven or eight millimeter incision to be inserted into the eye. In contrast, a flexible or foldable lens can be manipulated and compacted to a much smaller size. Once compacted, the multi-component intraocular lens can be delivered using a relatively smaller incision, for example, about three millimeters or less. By using a smaller incision, the patient reaps optical and practical benefits. From an optical standpoint, any time incisions are made to the cornea, the cornea loses some of its natural globularity due to imperfections caused by the incisions and the resultant trauma. The imperfections in the cornea lead to induced astigmatism, or optical aberrations caused by irregularities in the shape of the cornea. By minimizing the size of the corneal incision, a surgeon may also minimize the amount of induced astigmatism. Even though the three-component design simplifies the process of correcting induced astigmatism, minimizing the amount of induced astigmatism remains a primary goal for all intraocular surgeries.

As a practical matter, by making a smaller incision, the surgeon reduces the amount of actual trauma to the eye, thus reducing the occurrence of complications and decreasing the time for recovery. These advantages are further realized if the surgeon is able to perform the intraocular surgery using an incision small enough to heal without the use of stitches, wherein the incision is small enough to allow the eye's natural ocular pressure to hold the incision together during the healing process.

The inventor's application Ser. No. 11/698,875 overcame the above-described drawbacks of the related art. FIGS. 12-16 illustrate the invention disclosed in the '875 patent application.

For example, FIG. 12A shows a top or plan view of an intraocular foldable base lens 100, which is similar to the MC-IOL base lens illustrated in FIG. 3. The base lens 100 attaches to the eye by at least one haptic 120 and while the base lens 100 in FIG. 12A can be secured to the eye by at least one haptic, it is preferable that at least two haptics 120 be used. As shown in FIG. 12A, each haptic 120 extends outward from the base lens 100, and is tilted from between 10 to 20 degrees, in either direction, relative to a plane taken across the base lens, preferably having a 15 degree positive tilt.

As shown in FIG. 12B, the base lens 100 can also include one or more flanges 105 disposed on and extending outwardly away from the body of the base lens 100. Each flange 105 can also have a slot 110 designed or configured to receive or accept an assembly of a top lens 300 and a mid lens 200 therein.

The base lens in FIG. 13 is similar to the base lens 100 (FIGS. 12A-12B), except for a groove 130 being defined therein that extends along the entire outer periphery, and a plurality of attachment points 140, which serve to attach the optical region 150 to the base lens.

The foldable MC-IOL disclosed in the inventor's '875 application includes two or more additional refractive components, i.e., a top lens 300 and a mid lens 200. The mid lens 200, which typically allows spherical adjustments, is illustrated in FIGS. 14A-14B, while the top lens 300 (FIG. 15) carries the astigmatic correction and has an orientation projection 305. The mid lens 200 may include at least one projection 210 extending away from the body of the mid lens 200 and may have varying lengths depending on the shape and number of projections. The mid lens 200 also includes a side portion 250 which extends upward, and terminates at a lip 225, as illustrated in FIG. 14B. The side portion 250 and lip 225 extend along the outer circumference of the mid lens 200, thereby defining a notch 230.

Prior to insertion into the eye, the top lens 300 engages the notch 225 of the mid lens, such that a seal is formed between the notch 225 and the top lens 300, and which holds the mid lens 200 and the top lens 300 together as a single assembly. The top lens 300 is oriented so that, when the top lens 300 is inserted into the mid lens 200, raised projections or notches 305 of the top lens 300 face the mid lens 200 or may also project away from the mid lens 200. The notches or projections 305 can provide directional and axial orientation for the top lens, similar to the axis orientation marks 85 of FIG. 5.

The surgeon performing the operation or the lens manufacturer assembles the mid lens 200 and the top lens 300 outside the eye to a predetermined axis orientation to correct the astigmatism, and then inserts the completed assembly into the eye as one folded piece such that the mid lens 200 is sandwiched between the base lens 100 and top lens 300. The surgeon inserts the top lens 300 and the mid lens 200 assembly into the base lens 100 by sliding a projection 210 of the mid lens 200 into a slot 110 of a corresponding flange 105 of the base lens 100. Once the first projection 210 is in place in the corresponding first slot 110, if more projections are present in the mid lens 200, then the surgeon adjusts the mid lens 200 and the top lens 300 until the other projection(s) 210 line up with the other slot(s) 105. Once all projections 210 have been inserted into their corresponding slots 110, the assembly of the top lens 300 and the mid lens 200 is secured in the base lens 100, and the procedure is completed.

In the event that the assembly formed by the mid lens 200 and the top lens 300 requires replacement, the surgeon may perform a disassembly procedure as discussed herein. First, a cannula containing visco elastic material would be introduced into the eye and positioned at the interface between the lens assembly (mid lens 200 and top lens 300) and the base lens 100. The injection of visco elastic causes the mid 200/top 300 lens assembly to elevate, thus disengaging the projections 210 from the slots 110 in the base lens 100. The original lens assembly would then be removed from the eye, and a new lens assembly placed into the eye and attached to the base lens 100 similar to as described above in the primary operation.

SUMMARY OF THE INVENTION

It is an aspect of this invention to provide a multi-component intraocular lens system with components that are removable and replaceable after placement in the eye.

It is an additional aspect of the present invention to provide a multi-component intraocular lens system with foldable components in order to minimize trauma to the eye. Trauma is minimized by allowing the use of a delivery system for the foldable lens which requires an incision smaller than the unfolded diameter of the foldable lens.

It is a further aspect of this invention to provide a multi-component intraocular lens system with components designed to simplify the surgical procedure for intraocular lens component insertion. An embodiment of the present invention includes a multi-component intraocular lens, wherein the base lens is attached with haptics, and the top and mid lenses are assembled outside the eye.

Furthermore, the present invention provides a different orientation of the mid lens and top lens than the orientation disclosed in the inventor's '875 application.

Specifically, an embodiment of the present invention includes inverting or reversing the order of the mid lens and top lens such that the top lens is placed on top of the base lens and the mid lens then positioned on top of the top lens such that the three components are oriented in an order where the base lens is most posterior relative to the patient's eye. The top lens is then placed on the base lens and the mid lens arranged on the top lens such that the mid lens is most anterior relative to the patient's eye and the top lens is arranged between or in the middle of the base and mid lens.

Moreover, while the inventor's application Ser. No. 11/698,875 teaches the mid lens includes a notch with which a projection of the top lens engages to securely maintain the mid/top lens assembly, an embodiment of the instant application provides the top and mid lenses being joined to each other by a joining means, such as, for example, a medical adhesive that is applied in at least one location where the mid lens interfaces with the top lens.

Further, the present invention includes a feature wherein the haptic of the mid lens has projections extending anteriorly and posteriorly that capture the top lens (circular configuration) and retain the top and mid lens (circular configuration) as an optical assembly. The dual direction extending projections allow the surgeon or manufacturer the ability to orient the components independently at each of 360° orientations. Each of the circular components (i.e., the mid lens and top lens) can be used to correct sphere cylinder presbyopia, spherical aberrations, and higher order aberrations.

Also, the present invention includes an embodiment wherein the mid and top lenses are integrated into a single component such that an adhesive or other such joining mechanism is not necessary to join the mid and top lenses together.

Moreover, the front lens or optical assembly can be custom manufactured into a single piece for each patient to correct sphere cylinder presbyopia, spherical aberrations, and higher order aberrations The intraocular lens system of the present invention allows assembly without the use of special equipment or techniques for securing the top and mid lenses together.

It is an aspect of the present invention to provide a modified multi-component intraocular lens implanted in an optical system of a human eye, including three or more removable components, with each component being foldable, and two of the removable components being connected to each.

BRIEF DESCRIPTION OF THE FIGURES

In the drawings:

FIGS. 5A-5B are top and side views, respectively, of a type of compound intraocular lens-top lens component;

FIGS. 18A and 18B are an exploded top view and an exploded side view, respectively, of the top lens replaceable component of a foldable multi-component intraocular lens according to an embodiment of the present invention;

DETAILED DESCRIPTION OF THE PREFERRED EMBODIMENT

Figure 1:
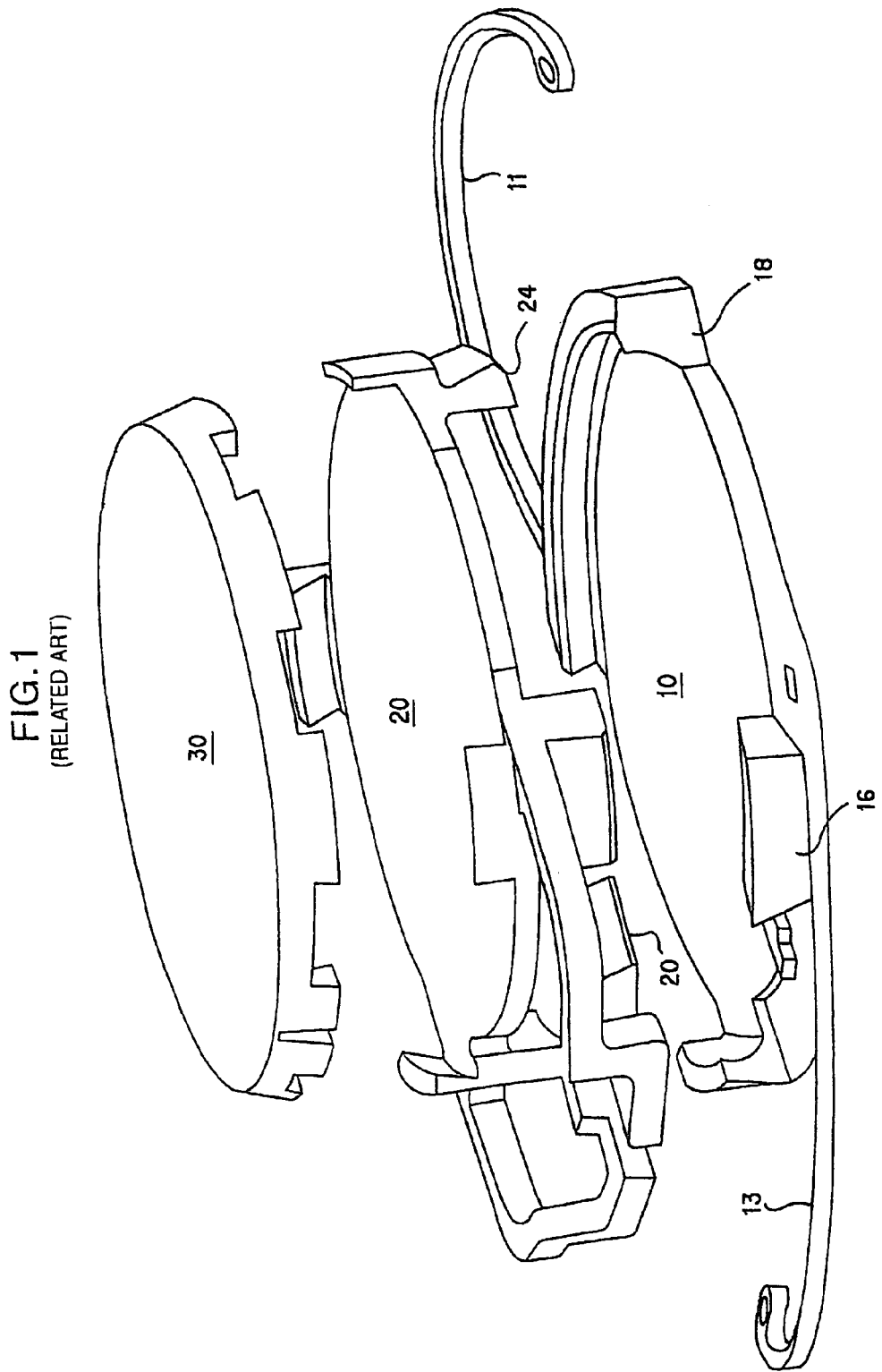
FIG. 1 is a plan view of the base, mid, and top lens components of a currently known multi-component intraocular rigid lens.
Figure 2:
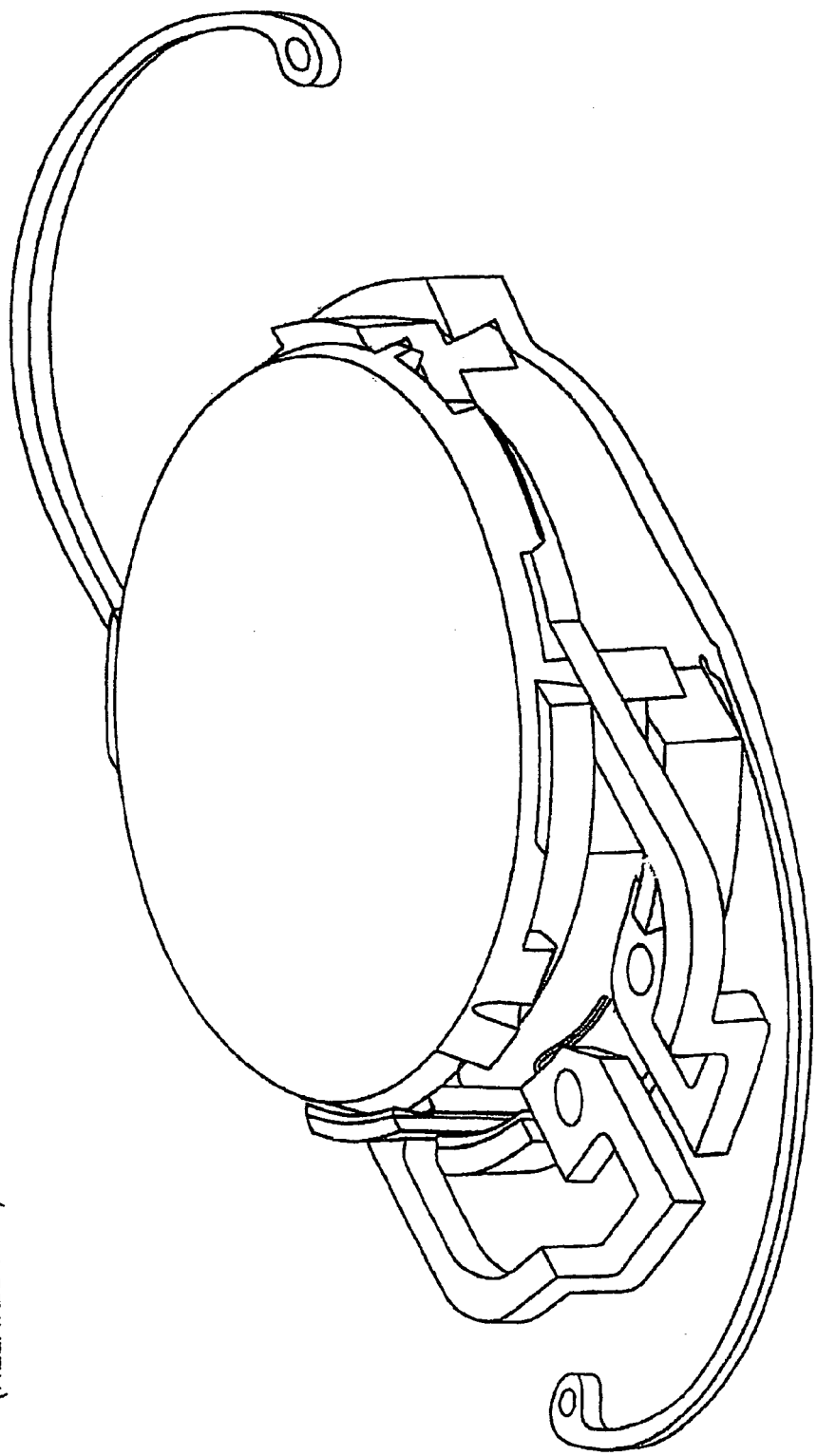
FIG. 2 is an exploded side view of the assembled base, top, and mid lenses of the currently known multi-component intraocular rigid lens shown in FIG. 1.
Figure 3A:
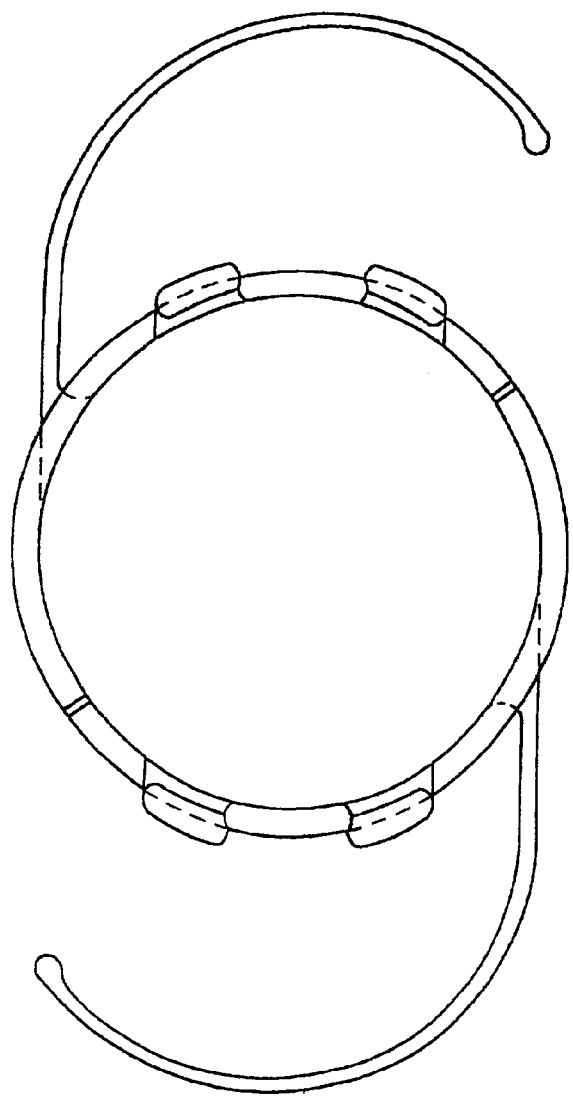
FIGS. 3A-3B are exploded views of a two component compound intraocular lens.
Figure 3B:
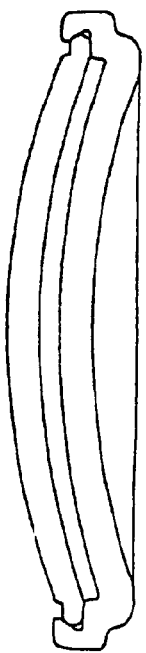
Figure 4A:
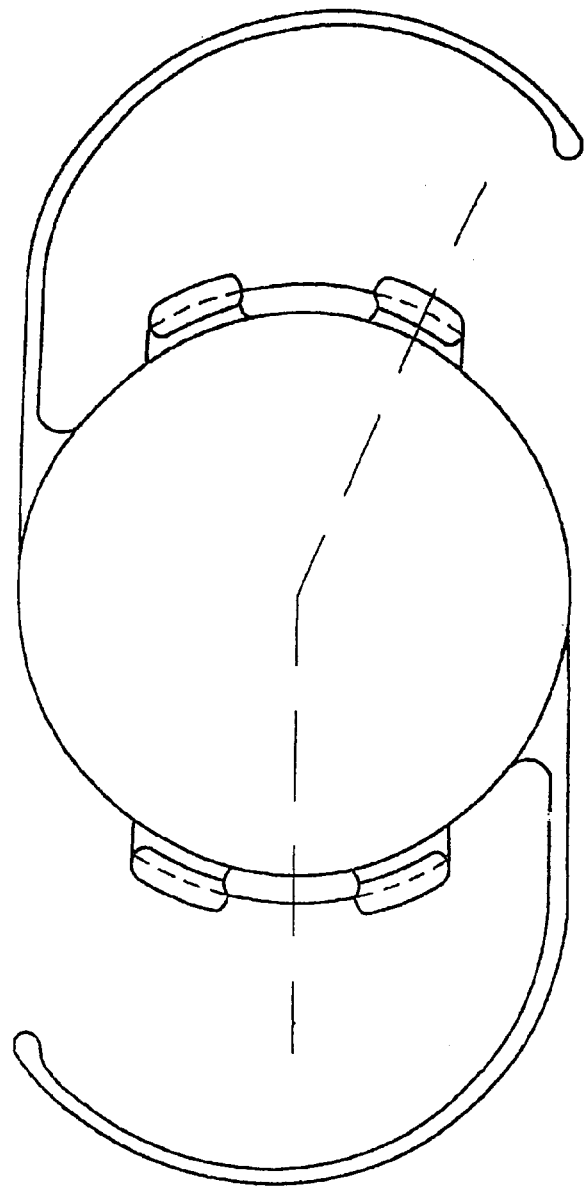
FIGS. 4A-4B are top and side views, respectively, of a type of compound intraocular lens-top lens component.
Figure 4B:
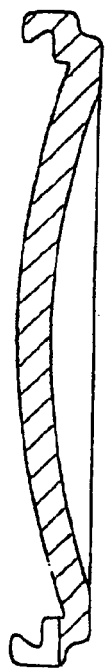
Figure 6:
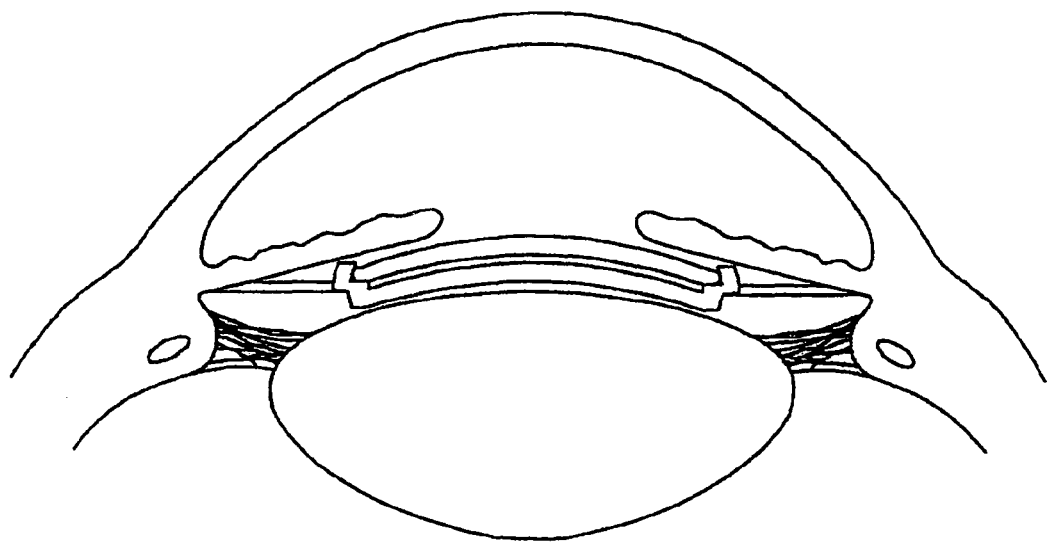
FIG. 6 is a side view of a compound intraocular lens implanted within a human eye ciliary sulcus.
Figure 7:
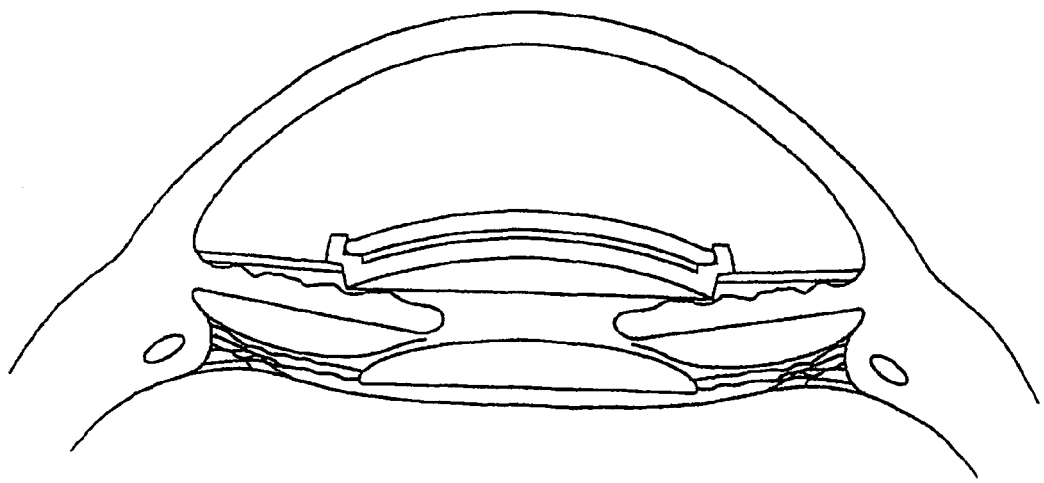
FIG. 7 is a side view of another compound intraocular lens implanted within a human eye using the anterior chamber angle as support.
Figure 8:
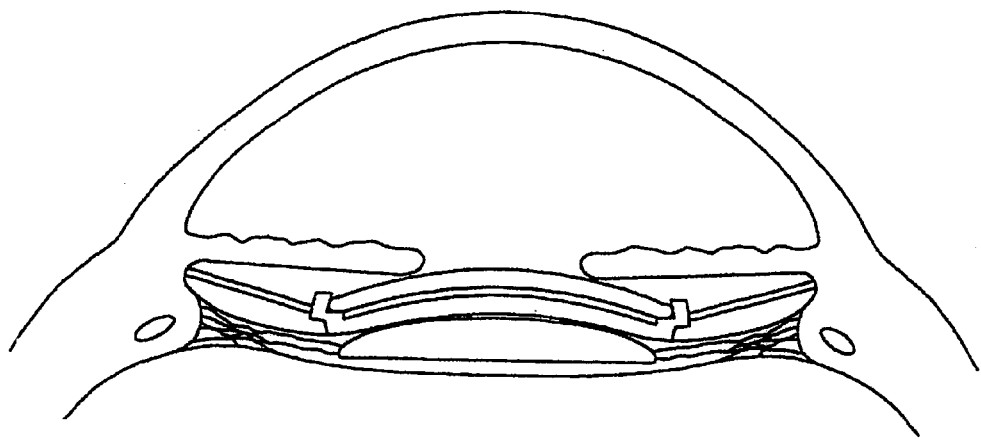
FIG. 8 is a side view of a sulcus mounted compound intraocular lens implanted within a human eye with a previously implanted single component conventional intraocular lens mounted in the capsular bag.
Figure 9:
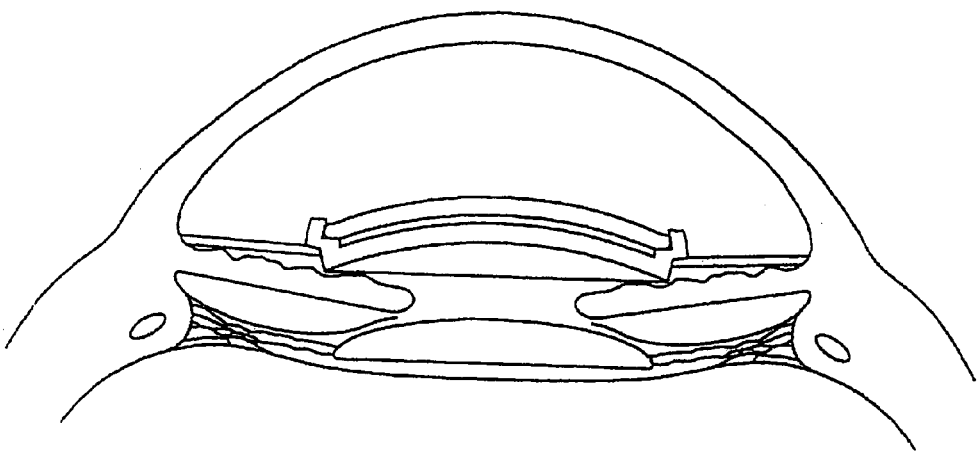
FIG. 9 is a side view of an anterior chamber mounted compound intraocular lens implanted within a human eye with a previously implanted single component conventional intraocular lens mounted in the capsular bag.
Figure 10:
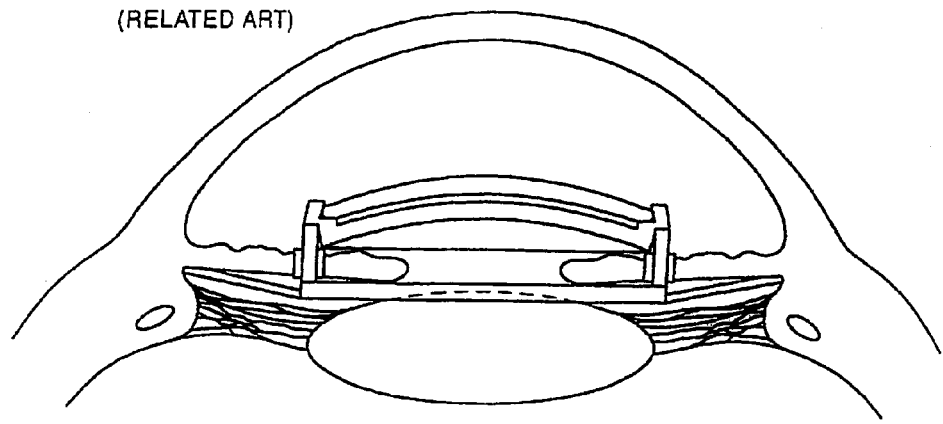
FIG. 10 is a side view of an anterior chamber mounted compound intraocular lens on a support secured in the posterior chamber and is implanted within a human eye with a previously implanted single component conventional intraocular lens mounted in the capsular bag.
Figure 11:
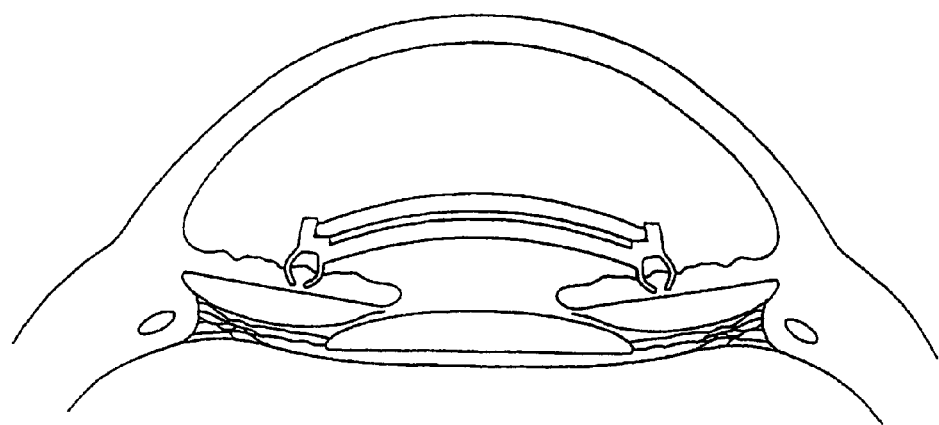
FIG. 11 is a side view of an iris fixated compound intraocular lens in the anterior chamber that is implanted within a human eye with a previously implanted single component conventional intraocular lens mounted in the capsular bag.
Figure 12B:
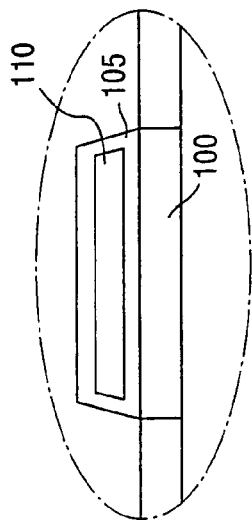
FIG. 12B is a side view of an enlarged portion of the base lens shown in FIG. 12A.
Figure 12A:
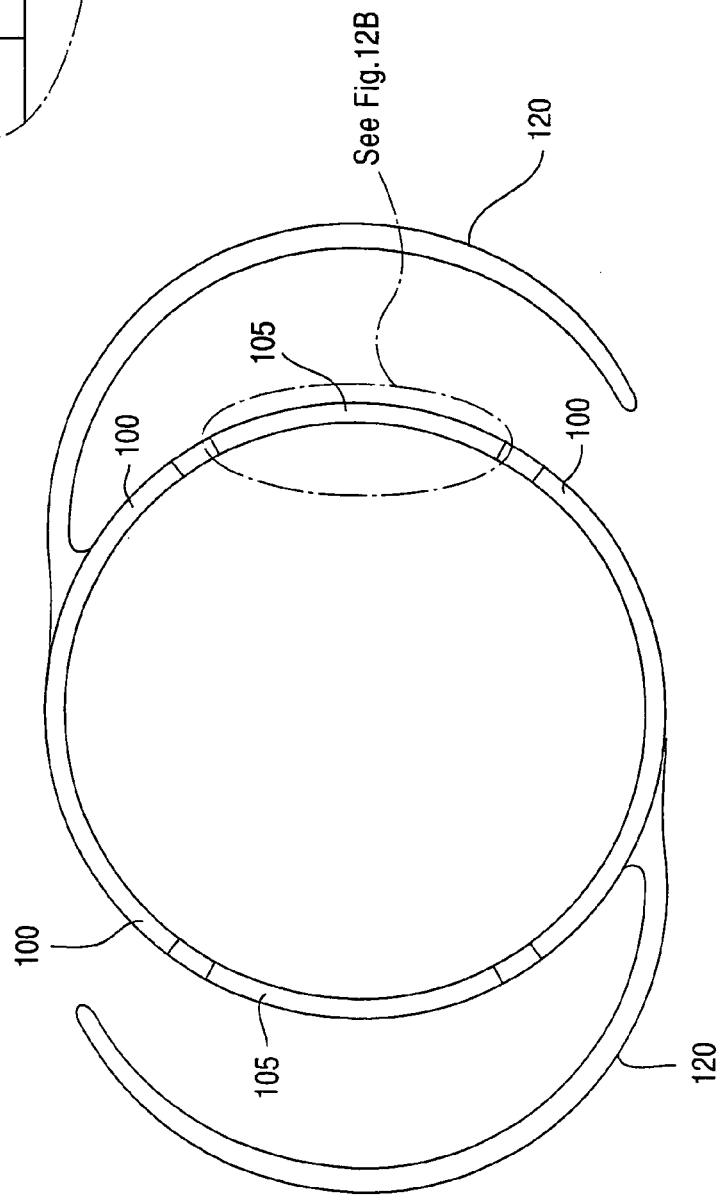
FIG. 12A is a top view, with an enlarged side view cutaway, of the base component of a foldable multi-component intraocular lens.

It should be noted that according to the preferred embodiments of the present invention, the fully assembled or end appearance of the base lens 100' of the present invention compared to the base lens 100 described above and illustrated in FIGS. 12A, 12B and 13 is substantially similar to the base lens 100 disclosed in the '875 application. Therefore, a detailed description of many of the common features of the base lens 100' with the base lens 100 is omitted herefrom in order to avoid redundancy.

However, it should be noted that the base lens 100' of the present invention differs from the above-described base lens 100 in that the base lens 100' is initially manufactured to be in three components that are to be assembled together and haptics 120' in the base lens 100' are configured to be a plate shape haptic 120' as opposed to the C-loop haptic 120 in the above-described base lens 100. The plate shaped hepatic 120' (FIG. 24) is configured to have ears 121', 121' which are enveloped and retained by the eye tissues of the patient.

Figure 17A:
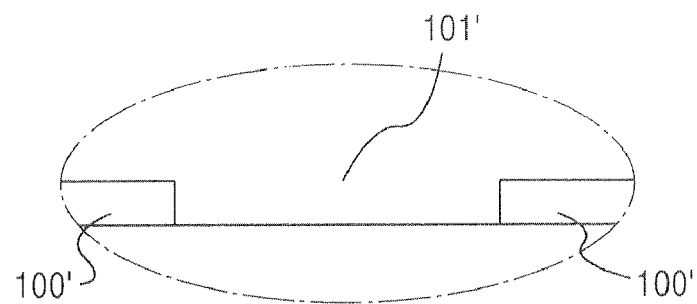
FIGS. 17A-17C are exploded views detailing the assembly process of the flange with the base lens component of a foldable multi-component intraocular lens according to an embodiment of the present invention.
Figure 17B:
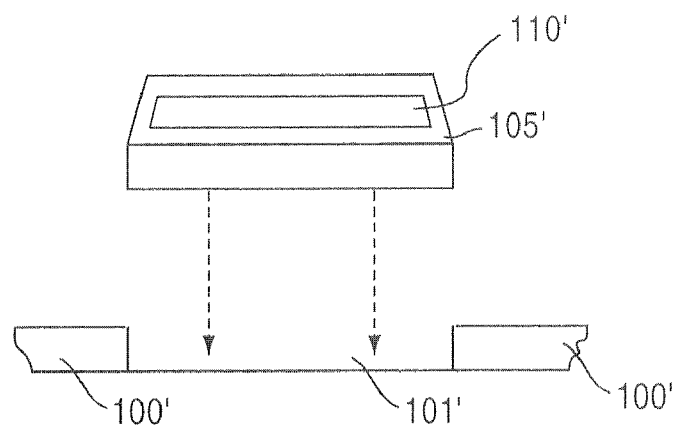
Figure 17C:
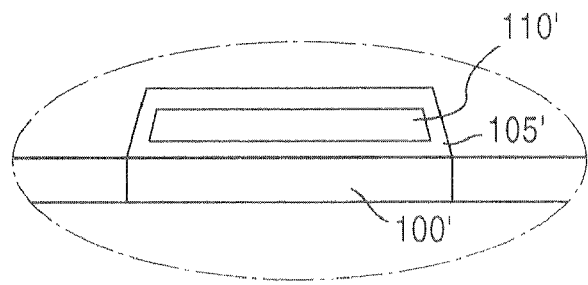

Moreover, as shown in FIG. 17A, a notch 101' (or cutout or depression) is formed in at least one and preferably two locations of a body of the base lens 100' that diametrically oppose each other across the body of the base lens 100' (only one notch 101' is illustrated). Then, as shown in FIG. 17B, a flange 105' (or vertical projection) is configured to engage or be inserted into the notch 101'. It should be noted that the flange 105' is previously manufactured to have a slot 110' defined therein. The flange 105' is snug or snap fit into the notch 101' and can mechanically be held therein to form the base lens 100' (FIG. 17C). It is also within the scope of the present invention for the flange 105' to be held in the notch 101' by other conventional and well-known techniques for joining two components of an apparatus, such as, for example only, placing an adhesive or glue in discrete locations along a perimeter of the notch 101' or along the entire perimeter of the notch 101' to join the flange 105' to the base lens 100' at the notch 105', or using a laser to join the flange 105' to the base lens 100', or ultrasonically welding the flange 105' and base lens 100' together, or any other suitable technique that is now known or later developed. It should be noted that it is also within the scope of the present invention for the slot 110' to be formed in the flange 105' by cutting the opening of the slot 110' using a laser.

As in the disclosure of the '875 application, the foldable MC-IOL according to the present invention also includes two or more additional refractive components, including an assembly of a mid lens 300' and a top lens 200', described more fully herein. It should be noted that the top lens 300 and the mid lens 200 of the '875 application are similar to the mid lens 300' and top lens 200' described below, with the exception of certain key differences.

A key difference between the disclosure of the '875 application and the present invention is the orientation of the top lens 300 and the mid lens 200. In the '875 application, the mid lens 200 was disposed between the base lens 100 and the top lens 300. In the instant application, the top lens 300 is now the mid lens 300' and the mid lens 200 is now the top lens 200'.

One embodiment of the top lens 200' is illustrated in FIGS. 18A and 18B. The top lens 200' allows spherical adjustments from −4.00 D to +4.00 D in 0.25 D increments. In an embodiment of the present invention, the mid lens 300' carries the astigmatic correction, which can range, for example, from 0.00 D to 5.00 D cylinder in 0.25 D increments and has an orientation projection 305. The present values are presented merely for illustrative purposes, and other possible ranges for the cylinder and the sphere values are considered to be within the scope and pervue of the invention.

Like the base lens 100, the mid lens 300' may be constructed from acrylic, silicone, or any other material suitable for manufacturing a foldable intraocular lens. The mid lens 300' has a central thickness ranging from 0.1 millimeters to 0.4 millimeters, and a diameter ranging from 1.50 to 8.50 millimeters, but preferably is between 5.50 and 7.00 millimeters. The mid lens 300' features an optical aperture ranging from 3.0 millimeters to 7.0 millimeters, with a preferable optical aperture of 5.5 millimeters.

The top lens 200' and/or the mid lens 300' may serve multiple purposes depending on the specific embodiment and the specific nature of the problem to be solved. For example, the mid lens 300' and/or the top lens 200' may correct myopia, presbyopia, astigmatism, spherical aberrations and other higher order aberrations. The mid lens 300' and/or the top lens 200' may also be used to correct cosmetic defects in the eye. The mid lens 300' and/or the top lens 200' may also be tinted to protect the eye from ultraviolet rays, or blue light, or to reduce glare, or to change the color of the eye for cosmetic or other purposes. The mid lens 300' and/or the top lens 200', like the base lens 100, may also be constructed in a manner which allows the mid lens 300' and/or the top lens 200' to absorb light in the ultraviolet wavelength portion of the light spectrum, for the purpose of achieving the same goals as mentioned above.

In an embodiment of the present invention, the mid lens 300' and/or the top lens 200' may be designed to change the light-gathering aspects of the eye to improve night vision. A lens with these characteristics has potential use for military applications, such as low light or telescopic use, or for underground workers, or in any other application where the patient desires reversibly enhanced night vision, or vision enhancement in a specific area of the spectrum. For example, athletes such as baseball players may desire amber-tinted lenses to improve their ability to perform the tasks critical to their sport, such as seeing the ball. Lenses designed for this purpose could be removed when the patient no longer desires the enhanced vision characteristic, for example when the military application is finished, or the athlete's season or career ends.

In another embodiment of the present invention, the mid lens 300' and/or the top lens 200' may be used to deliver pharmacological compounds, such as medicines, into the eye. The mid lens 300' and/or the top lens 200' in this embodiment feature a system for delivering a compound into the eye over a predetermined period of time. At the end of the predetermined time period, the surgeon removes the mid lens 300' and/or the top lens 200', and replaces the mid lens 300' and/or the top lens 200' with a new lens for delivering a compound into the eye, if needed. In this way, the patient may conveniently receive delivery of a compound directly into the inner portions of the eye, while minimizing the risk to the patient, and simplifying the delivery of the compound. Because this treatment does not require recurring action by the patient, the treatment avoids the problem of patient non-compliance, which is critically important to the treatment of chronic eye disorders, such as glaucoma, diabetes, and macular degeneration.

Figure 14B:
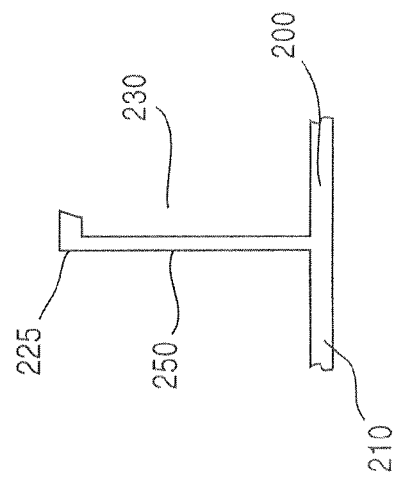
FIGS. 14A and 14B are an exploded top view and an exploded side view, respectively, of the mid lens replaceable component of a foldable multi-component intraocular lens.
Figure 14A:
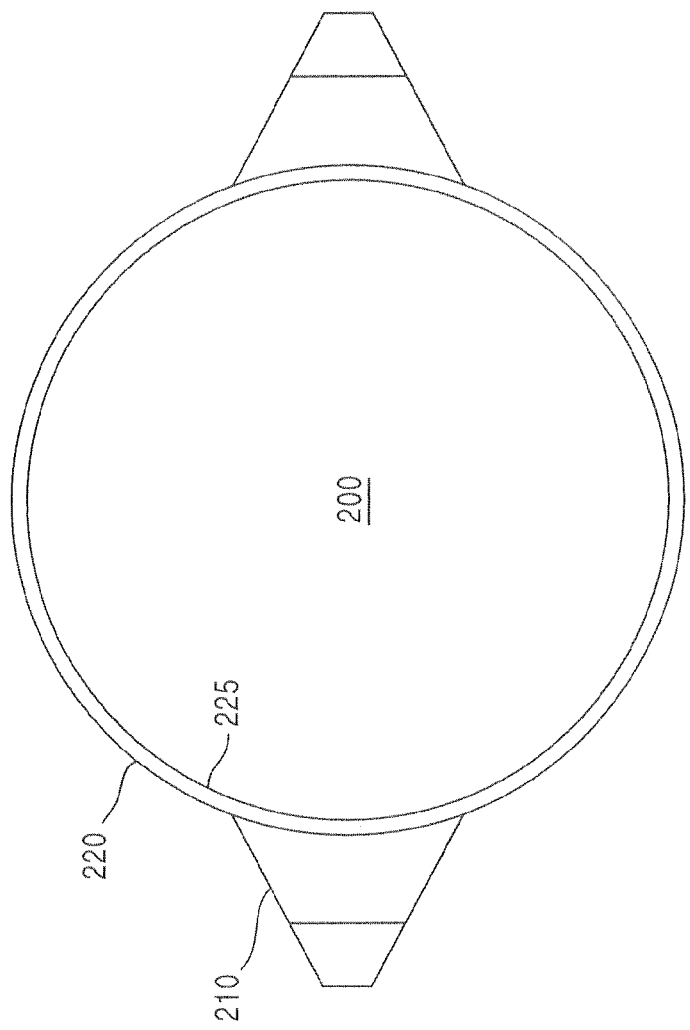
Figure 15:
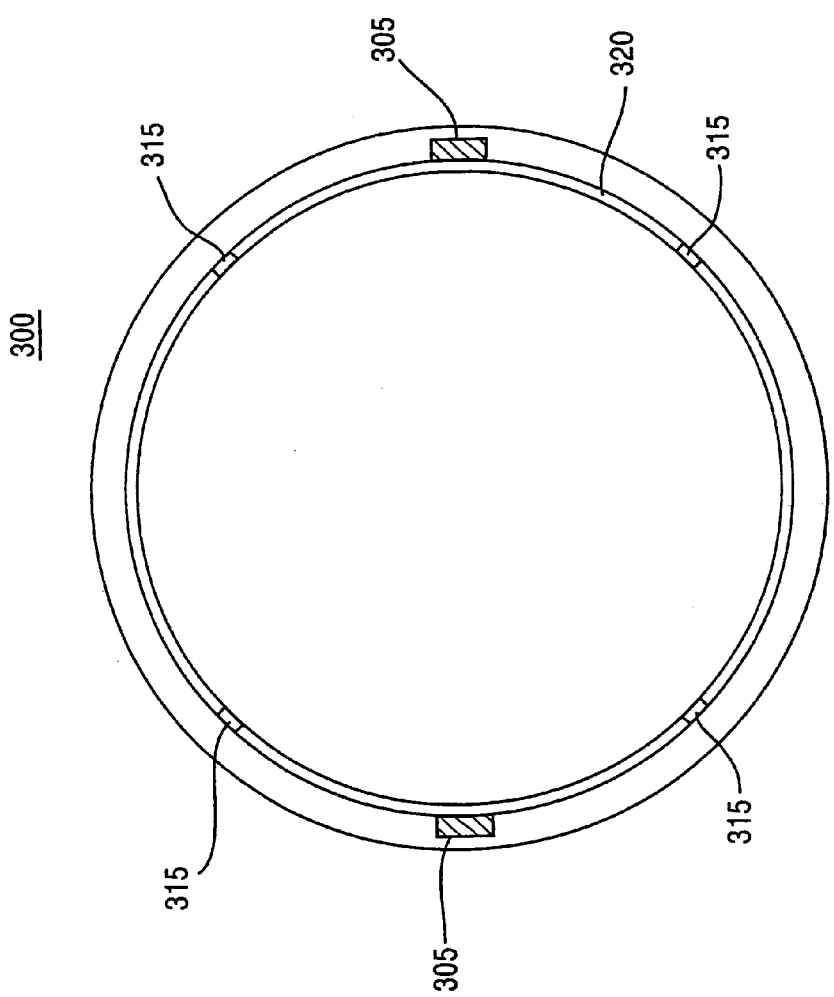
FIG. 15 is an exploded top view of the top lens component of a foldable multi-component intraocular lens.

FIG. 18A illustrates a top view of the top lens 200' of an embodiment of the present invention. As in the mid lens 200 (FIG. 14A), the top lens 200' includes one or more projections 210 extending horizontally from the body of the top lens 200', preferably in the plane parallel to the edge of the top lens 200', but optionally at any angle from 150 to 180 degrees in either direction. Each projection 210 may extend outward from the lens ranging from 0.5 to 5.0 millimeters from the outer edge of the top lens 200'. Each projection 210 may also have varying lengths depending on the shape and number of projections. The projections 210 are illustrated in FIG. 18A as trapezoidal, but any shape which would accomplish the stated purpose of fitting into slot 110' of the flange 105' extending from the base lens 100', for example, rectangular, triangular, half-oval, notched, ridged, serrated, or any other suitable geometric shape, is considered to be within the scope and pervue of the present invention. Additionally, any shape, indentation, marking, notching, or surface treatment of the flange 105', including, for example, ribbing, roughening, adding bumps, notches, and indentations, are considered to be within the scope and pervue of the present invention. Likewise, the use of any adhesive material on the flange, for example, glues, Velcros™, cements, resins, pastes, or any other adherent, is also considered to be within the scope and pervue of the present invention.

As shown in FIG. 18B, the top lens 200' also comprises a side portion 250' which extends away from, both anteriorly and posteriory or up and down as viewed in the figure, and along the outer circumference of the top lens 200'. The top lens 200' includes an inner surface 250a that defines an interface region where the inner surface 250a of the side portion 250' receives a medical adhesive MA that will securely retain the mid lens 300' thereto in order to define a top lens 200'/mid lens 300' assembly.

Prior to insertion into the eye, the medical adhesive MA is applied to the inner surface 250a of the top lens 200'. It should be noted that the medical adhesive MA may be applied to completely cover the entire surface area of the inner surface 250a as will be described in further detail below, or less than the entire surface area. The minimum amount of medical adhesive to be applied to the inner surface 250a should be sufficient to securely retain the mid lens 300' in the top lens 200'.

The medical adhesives MA may be selected from one of a group including cyanoacrylate adhesives, which may be applied with or without cyanoacrylate accelerators and primers, light cure acrylics, light cure cyanoacrylates, light cure silicones, epoxy adhesives, and any other adhesive that is suitable for the present invention. Although not a requirement, it is preferable that whichever adhesive is selected, that the medical adhesive MA be capable of curing under either UV or visible light sources and respond to low, medium or high intensity light.

Figure 19:
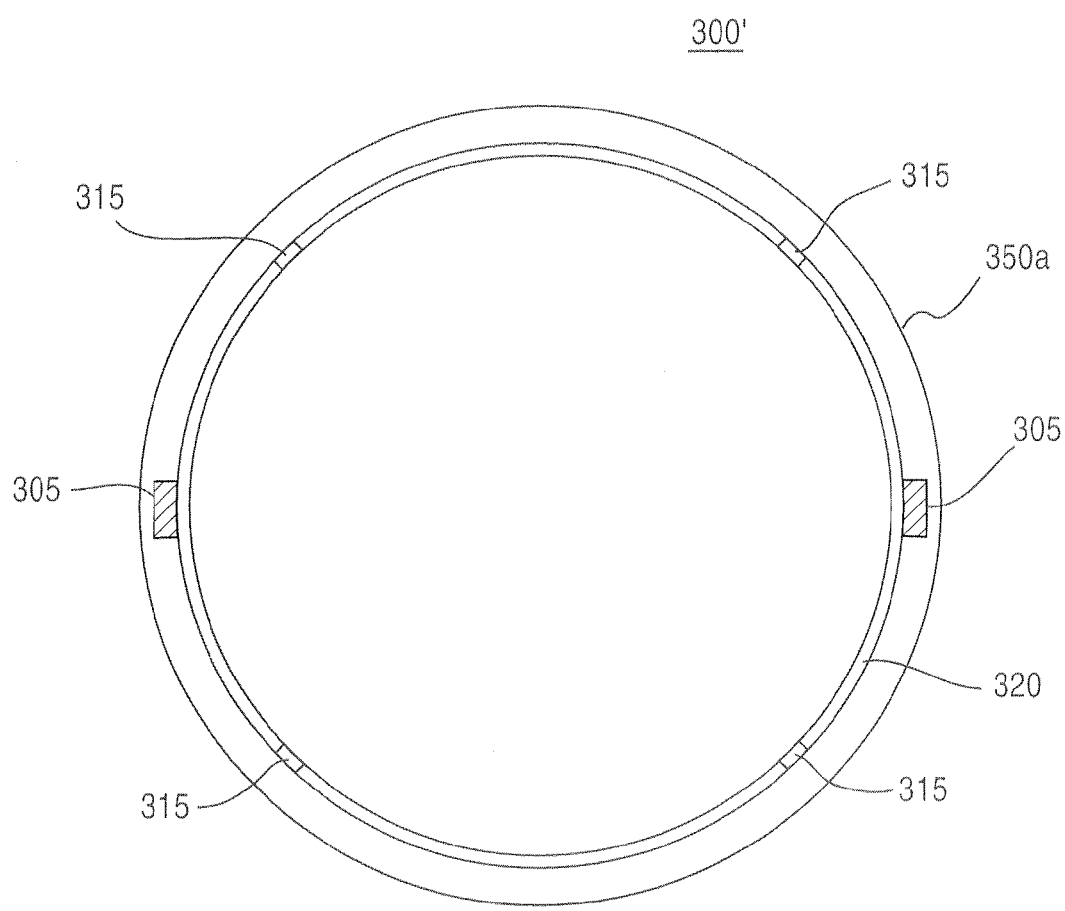
FIG. 19 is an exploded top view of the mid lens component of a foldable multi-component intraocular lens according to an embodiment of the present invention.

An opposing side surface 350a of the mid lens 300' engages the inner surface 250a of the side portion 250' and is retained there by the medical adhesive MA such that a seal is formed between the side portion 250' of the top lens 200' and the side portion 350a of the mid lens 300', and which holds the top lens 200' and the mid lens 300' together as a single assembly. Like the top lens 300 of the '875 application, the mid lens 300' of the present invention includes a groove 320 defined in a surface of the mid lens 300', and extends along the circumference of the outer periphery of the mid lens 300'. The groove 320 extends along the circumference of the mid lens 300', except for the location of the compression slots 315, as shown in FIG. 19. Although four compression slots 315 are illustrated here, embodiments with more compression slots or fewer compression slots are also considered to be within the scope and pervue of the invention. Groove 320 and a series of compression slots 315 allow for an easier engagement of the mid lens 300' with the top lens 200'. In other embodiments, the groove 320 could be replaced with other slots or channels defined in the periphery of the lens, and the invention should not be considered to be limited to this specific embodiment.

The mid lens 300' also includes one or more end notches 305. In FIG. 19, two end notches 305 are illustrated, but varying numbers of end notches, or no end notches at all, are considered to be within the scope of the invention. The end notches 305 are raised slightly from the surface of the mid lens 300', and can be configured to be any one of notches, bumps, ridges, or indentations. The notches could also be of various shapes, sizes, and lengths. The mid lens 300' is oriented so that, when the mid lens 300' engages the top lens 200', the raised projections or notches 305 face the top lens 200' or may also project away from the top lens 200' and toward the base lens 100. The notches or projections 305 can provide directional and axial orientation for the mid lens, similar to the axis orientation marks 85 of FIG. 5.

Figure 16:
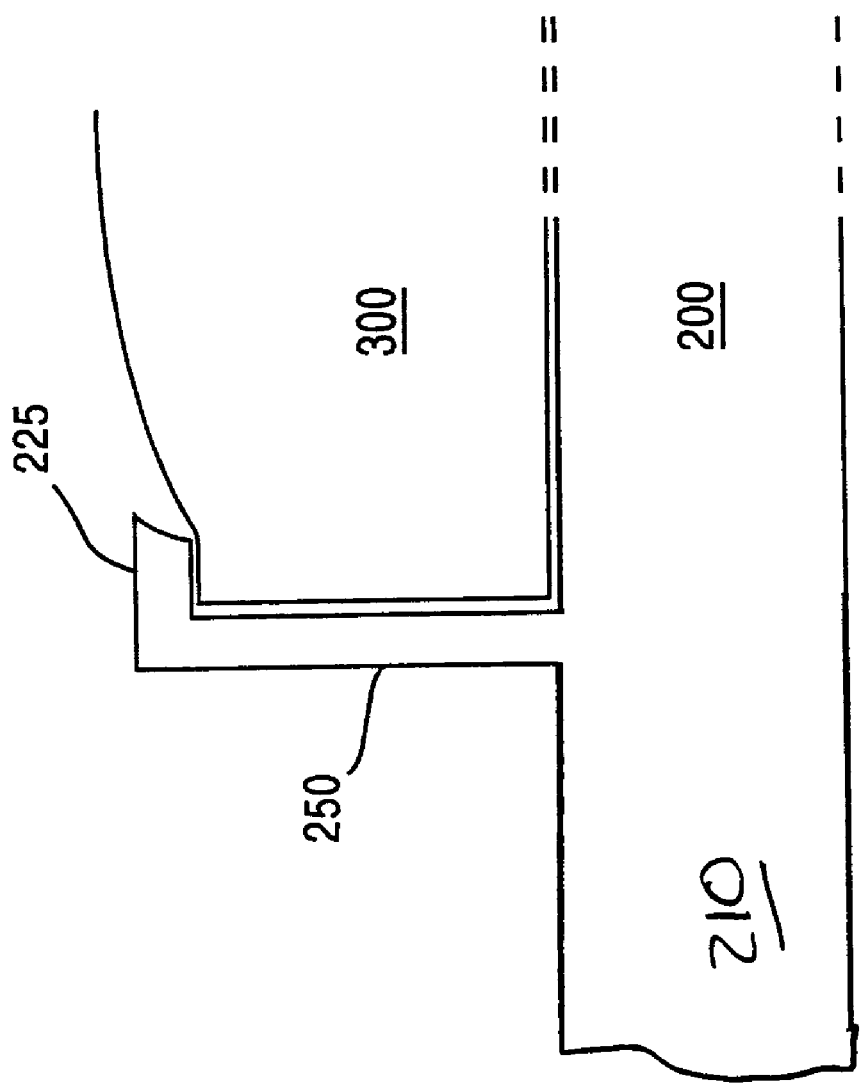
FIG. 16 is a side view of an optical assembly when the top lens is inserted into the mid lens.
Figure 20:
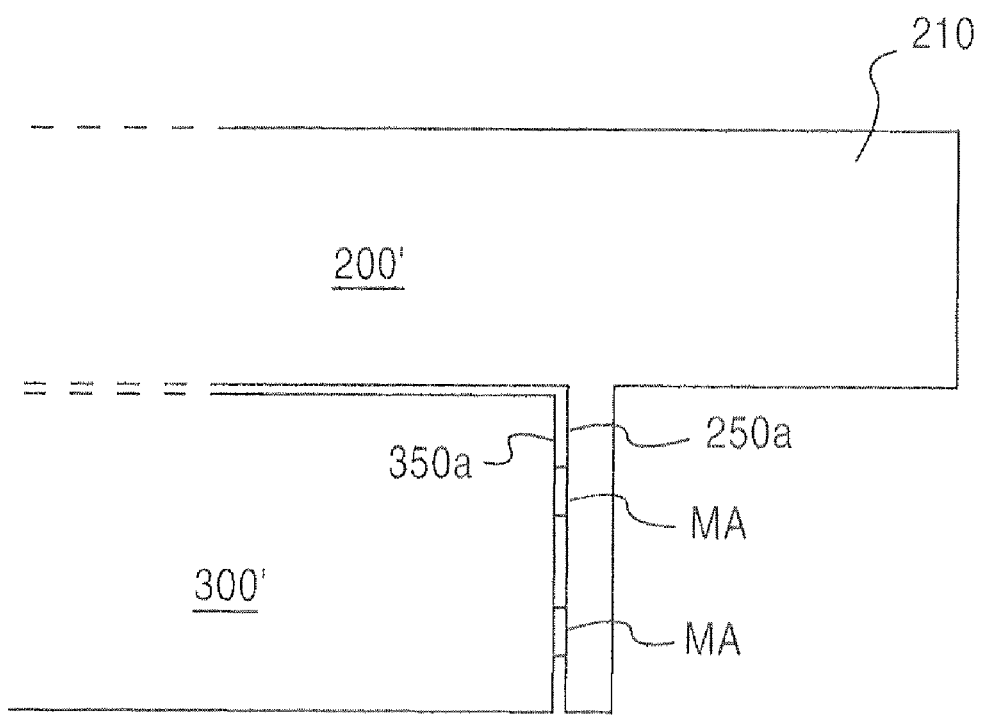
FIG. 20 is a side view of an assembly that is formed when the mid lens engages the top lens.

The surgeon performing the operation or the lens manufacturer assembles the top lens 200' and the mid lens 300' outside the eye to a predetermined axis orientation to correct the astigmatism, and then inserts the completed assembly into the eye as one folded piece. A side view of the completed assembly of the top lens 200' and the mid lens 300' is illustrated in FIG. 20. It should be noted that unlike the assembly shown in FIG. 16, the arrangement order of the mid lens 300' and the top lens 200' assembly of the present invention is reversed such that the mid lens 300', which is the top lens 300 in the '875 application, is not the mid lens 300' of the present invention, wherein the mid lens 200 of the '875 application is the top lens 200', such that the arrangement order of the present invention is base lens 100, mid lens 300' and top lens 200'.

It is noted that in FIG. 20, the sizes have been exaggerated in order to illustrate the relationship between the side surfaces 350a and 250a, respectively, of the mid lens 300' and the top lens 200'. It is also noted that, although in FIG. 20, the side surface 350a of the mid lens 300' is flush with the side surface 250a of the top lens 200', and the top portion of mid lens 300' is flush with the bottom portion of the top lens 200', this fitting is not required for the assembly of the mid lens 300' and top lens 200'. That is, embodiments in which the side surface 350a of the mid lens 300' is not flush with side surface 250a of the top lens 200' are considered to be within the scope and pervue of the invention.

Figure 21:
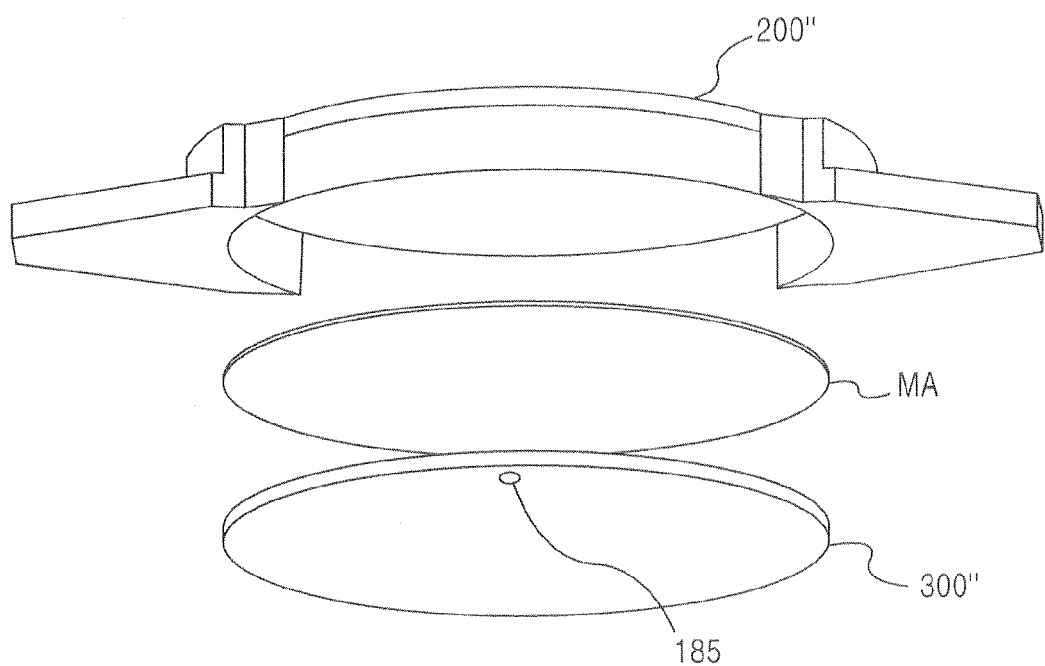
FIG. 21 is an exploded view of an optical assembly according to another embodiment of the present invention.
Figure 22:
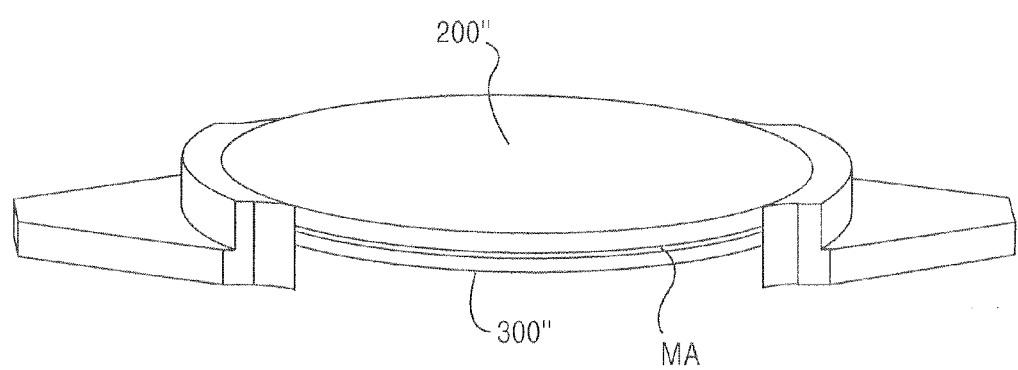
FIG. 22 is a perspective view of the optical assembly shown in FIG. 21 in the assembled state.
Figure 23:
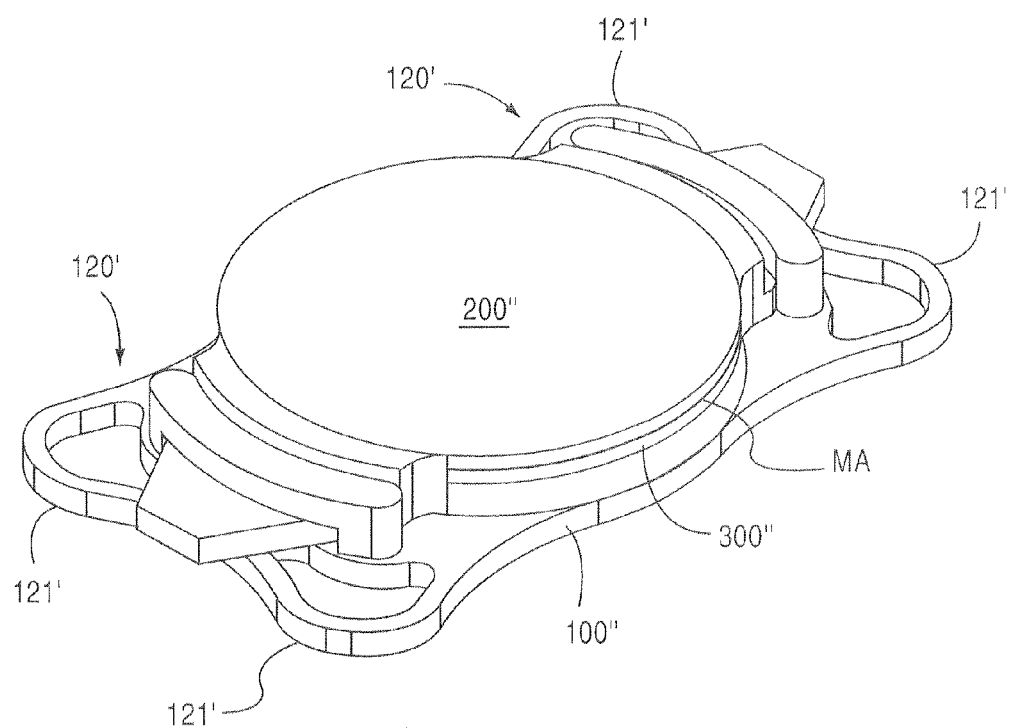
FIG. 23 is a perspective view of the optical assembly shown in FIG. 22 assembled with a base lens according to another embodiment of the base lens.

FIG. 21 illustrates an exploded view of another embodiment of the present invention wherein the medical adhesive MA is administered along an entire upper surface of the mid lens 300" and/or an entire lower surface of the top lens 200" which directly opposes the upper surface of the mid lens 300". It should be noted that in this embodiment, the mid lens 300" is provided with at least one projection for engaging the slot 110' formed in the flange 105' of the base lens 100' and, as such, the outer circumferential surface of the top lens 200" has a constant diameter. FIG. 22 illustrates an assembled state of the top lens 200" and the mid lens 300" with the medical adhesive MA joining the two lenses 200" and 300" together into a front lens assembly. As shown in FIG. 23, the front assembly (200" and 300") is then assembled with the base lens 100" which, in this embodiment, has the plate shaped haptic 120', wherein each haptic 120' has at least one pair of the previously discussed dog ears 121', 121'.

Once the base lens 100' has been inserted into and mounted within the eye, the surgeon inserts the mid lens 300' (300") and the top lens 200' (200") assembly into the base lens 100' by sliding a projection 210 into a slot 110' of a corresponding flange 105' of the base lens 100'. When attaching the assembly of the mid lens 300' (300") and the top lens 200' (200") to the base lens 100', the surgeon does not need to visually see the individual pieces line up together. Instead, the projection 210 is designed to slide into place with the slot 110'. That is, the surgeon unfolds the assembly of the mid lens 300' (300") and the top lens 200' (200"), and then slides the assembly across the base lens 100' until a first projection 210 lines up with a first slot 110'. Once a projection 210 lines up with a slot 110', the projection 210 catches in the slot 110', and the surgeon will feel the two pieces lock into place. Once the first projection 210 is in place in the corresponding first slot 110', if more projections are present in the top lens 200' (200"), the surgeon adjusts the top lens 200' (200") and the mid lens 300' (300") until the other projection(s) 210 line up with the other slot(s) 105'. Once all projections 210 have been inserted into their corresponding slots 110', the assembly of the mid lens 300' and the top lens 200' is secured in the base lens 100', and the procedure is completed.

In the event that the assembly formed by the top lens 200' and the mid lens 300' requires replacement, the surgeon may perform a disassembly procedure as discussed herein. First, a cannula containing visco elastic material would be introduced into the eye and positioned at the interface between the lens assembly (mid lens 300', 300" and top lens 200', 200") and the base lens 100'. The injection of visco elastic causes the mid lens 300' (300") and top lens 200' (200") assembly to elevate, thus disengaging the projections 210 from the slots 110' in the base lens 100'. The original lens assembly would then be removed from the eye, and a new lens assembly placed into the eye and attached to the base lens 100' similar to as described above in the primary operation.

While the invention has been described in conjunction with specific embodiments therefor, it is evident that various changes and modifications may be made, and the equivalents substituted for elements thereof without departing from the true scope of the invention. In addition, many modifications may be made to adapt a particular situation or material to the teachings of the invention without departing from the scope thereof. Therefore, it is intended that this invention not be limited to the particular embodiment disclosed herein, but will include all embodiments within the spirit and scope of the disclosure.

For example, the top lens 200' (200") may also have additional spherical power ranging from −9.50 D to 9.50 D in 0.25 D increments, and may be either monofocal or multifocal. The mid lens 300' (300") may also be constructed from acrylic, silicone, or any other material suitable for crafting a foldable intraocular lens. The top lens 200' (200") has a plano-convex lens with a central thickness ranging from 0.1 to 0.3 millimeters, and a diameter ranging from 1.5 to 8.5 millimeters, preferably between 6.0 and 6.5 millimeters, and an optical clear aperture ranging from 5.0 to 6.0 millimeters, preferably 5.5 mm. Similar to the base lens 100' and the mid lens 300' (300"), the top lens 200' (200") may also be manufactured in a manner to allow absorption of light in the ultraviolet wavelength portion of the light spectrum, or other portions of the light spectrum for which it may be clinically important to absorb light, such as the blue light portion.

Also, the top lens 200' (200") may have at least one bevel 210 formed along an outer edge thereof, allowing the top lens 200' (200") to fit into the opening 110 of the base lens 100'.

The three piece system (i.e. the base lens 100', the mid lens 300' (300"), and the top lens 200' (200")) described herein has a spherical power range of −20.00 D to +40.00 D and accuracy of +/−0.25 D. The three piece system has an adjustable cylindrical power of 5.00 D, and adjustable spherical power of +/−9.00 D. Its maximum central thickness is 1.88 millimeters, but could be as thick as 4.0 millimeters. The optical element diameter ranges from 1.00 millimeters to 8.00 millimeters. The optical aperture ranges from 3.0 to 7.0 millimeters, with an optimal optical aperture of 5.5 millimeters.

Any of the base, top, and/or mid lens components may be coated with chemicals to decrease their cellular reactivity, such as heparin or other surface passivation techniques to prevent building of cellular debris at the optical interface. Moreover, any of the lens components may be configured with a multifocal corrective component of any of several varieties: derefractive or refractive, bull's eye or aspheric, depending upon the desired optical characteristics. Additionally, extra components beyond the basic base, top, and mid components may be added to help with optical aberrations or other focusing refinements. In an embodiment of the present invention, additional top lenses may be added to the base lens 100', and attached in the same manner as the assembly of the mid lens 300' (300") and the top lens 200' (200") described above.

Figure 13:
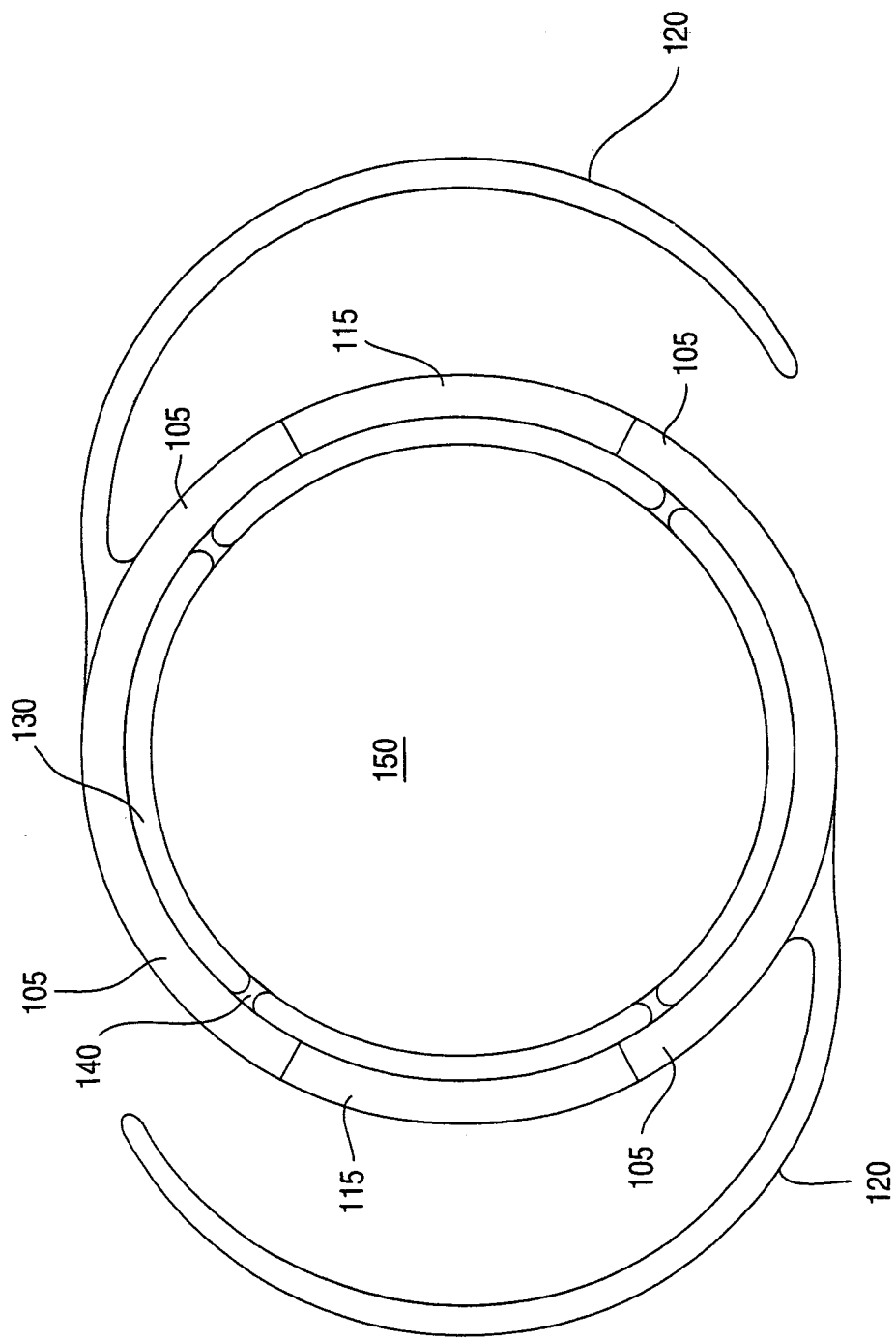
FIG. 13 is a top view of the base component of a foldable multi-component intraocular lens.

In another embodiment of the present invention, a telescopic lens can be introduced into the lens system for the treatment of macular degeneration. If the base lens 105 illustrated in FIG. 13 is used, then the surgeon can cut the attachment points 140 while the lens is in the eye, and remove the central optic 150 of the base lens 105. The surgeon can then implant a telescopic assembly, for example a Lipschitz telescopic assembly, in place of the optic portion of the base lens 105, to allow optical correction for macular degeneration.

By using specific predetermined combinations of lens powers for each of the three components, it is possible to achieve a large variety of possible corrective power while requiring only a minimum number of different lenses to be manufactured. By placing small degrees of spherical construction in each of the three optical components, a surgeon can, from a very limited inventory of lenses, construct all of the corrections needed to achieve optical powers from −20.00 D to +40.00 D of spherical correction, and from 0.0 to 5.0 D of cylindrical correction in any axis, all in standard 0.25 D steps.

Optical aberrations and abnormalities present after implantation of the intraocular lens are identified by measuring the optical system using, for example, wave front technology. A surface modifier may be used to modify either a surface of the eye itself, or a component of the intraocular lens system. If a component requires modification or replacement, the surgeon can remove the component, alter the component or replace it with another, and reinsert the component through the same wound which was used to implant the lens. This process is described more fully in U.S. Pat. No. 6,413,276, "Modified Intraocular Lens and Method of Correcting Optical Aberrations Therein," by the same inventor.

Figure 24:
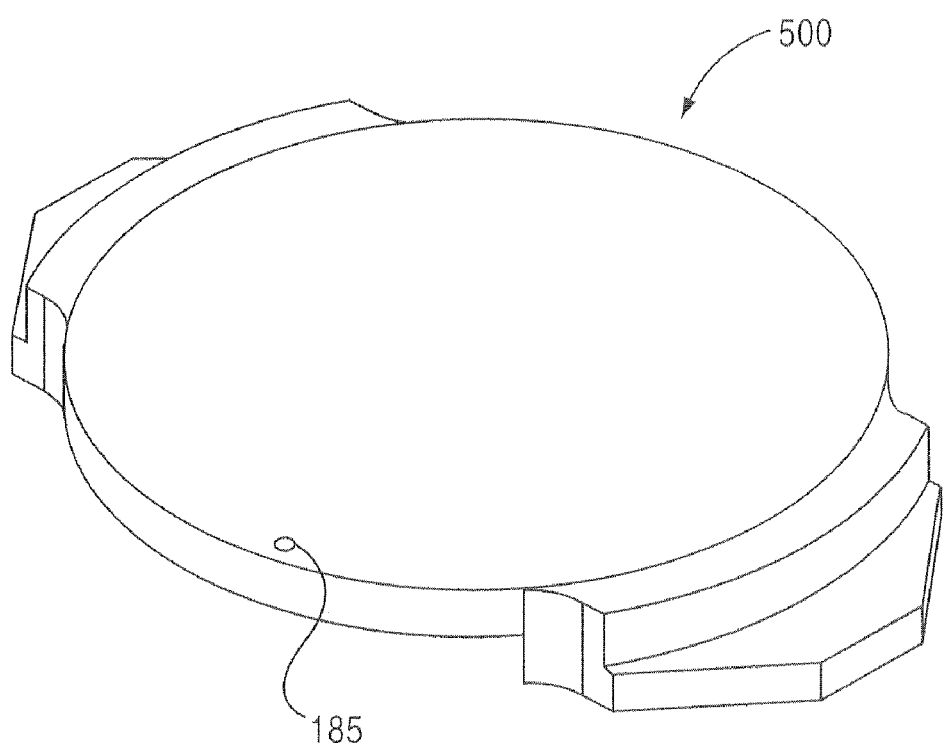
FIG. 24 is a perspective view of an optical assembly according to yet another embodiment of the present invention.
Figure 25:
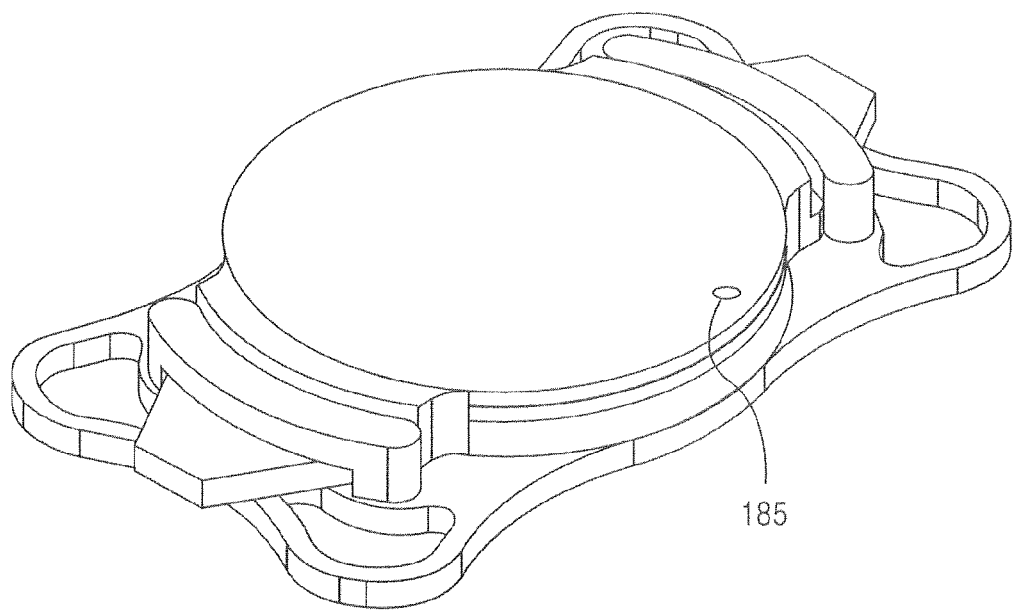
FIG. 25 is a perspective view of the optical assembly shown in FIG. 24 assembled with the base lens shown in FIG. 23

In yet another embodiment of the present invention, as shown in FIG. 24, the mid lens (300', 300") and top lens (200', 200") assembly can be prefabricated as a singe component or lens 500 that incorporates the two lenses as a single unit. The single component or lens 500 would preferably be manufactured to the patient's prescription and the lens 500 inserted into the base lens 100' as shown in FIG. 25. That is, the embodiment shown in FIG. 24 does not require the medical adhesive MA between the mid lens 300', 300" and the top lens 200', 200" because the mid and top lenses are integrated together to form the single piece lens 500.

Although not limited to the specific embodiment, FIGS. 20 and 24-25 the lens assemblies include at least one axis orientation mark 185 provided therein that provide the surgeon with assistance in terms of directional and axial orientation of the mid lens 300', 300" or lens 500 during the insertion procedure.

What is claimed is:

1. A multi-component intraocular lens implantable in an optical system of a human eye, comprising:

a base lens manufactured from a first foldable material, the base lens including at least one notch defined in a side portion of the base lens;

a flange attachable to the base lens; and an optical assembly manufactured from a second foldable material, wherein the flange is attached to the base lens by being inserted into the notch and includes an aperture defined therein through which the optical assembly passes to engage the base lens.

2. The intraocular lens of claim 1, wherein the flange securely engages the notch of the base lens by either one of an adhesive placed in discrete locations between the flange and the notch, a laser, ultrasonic welding, or a snap fit arrangement.

3. The intraocular lens of claim 1, further comprising at least one axis orientation mark provided thereon.

4. The intraocular lens of claim 1, wherein the optical assembly includes a first lens joined to a second lens.

5. The intraocular lens of claim 4, wherein the first lens is a top lens and the second lens is a mid lens.

6. The intraocular lens of claim 5, wherein a medical adhesive joins the top and mid lenses together.

7. The intraocular lens of claim 6, wherein the medical adhesive is applied to at least one of an outer circumferential surface of the top lens and an inner circumferential surface of the mid lens opposing the outer circumferential surface of the top lens.

8. The intraocular lens of claim 6, wherein the medical adhesive is applied to at least one of a top surface of the top lens and a bottom surface of the mid lens opposing the top surface of the top lens.

9. The intraocular lens of claim 6, wherein the medical adhesive is at least one of selected from a group including cyanoacrylate adhesives, light cure acrylics, light cure cyanoacrylates, light cure silicones and epoxy adhesives.

10. The intraocular lens of claim 5, wherein the mid lens carries an astigmatic correction and the top lens allows for spherical adjustments.

11. The intraocular lens according to claim 10, wherein the top lens is disposed between the mid lens and the base lens.

12. The intraocular lens of claim 5, wherein either one of the top lens and the mid lens comprises at least one projection extending away from an outer circumferential surface and which is configured to engage the aperture stet defined in the flange of the base lens.

13. The intraocular lens of claim 12, wherein the at least one projection is surface treated selected from the group of: notched, slotted, grooved, ridged, roughened, ribbed, gouged, striated, rifled, sulcated, corrugated, crimped, or canaliculated.

14. The intraocular lens of claim 12, wherein the at least one projection includes two projections, a first projection extending in a first direction and a second projection extending in a second direction that is different from the first direction.

15. The intraocular lens of claim 5, wherein at least one of the top lens and the mid lens is constructed with a predetermined cylinder and diopter value for correcting astigmatism.

16. The intraocular lens of claim 5, wherein at least one of the top lens and the mid lens includes a coating capable of blocking or absorbing a specific light wavelength or range of wavelengths.

17. The intraocular lens of claim 5, wherein at least one of the top lens and the mid lens is configured to deliver a pharmaceutical compound into an inner portion of the human eye.

18. The intraocular lens of claim 5, wherein at least one of the top lens and the mid lens is provided with a coating which enhances the human eye's ability to see particular area of a light spectrum.

19. The intraocular lens of claim 5, wherein the top lens is provided with a coating which enhances the human eye's ability to see at night.

20. The intraocular lens of claim 5, wherein at least one of the top lens and the mid lens, either alone or in combination with the other, is configured to correct at least one of sphere cylinder presbyopia, spherical aberrations, and higher order optical aberrations.

21. The intraocular lens of claim 1, wherein the aperture defined in the flange of the base lens has a shape selected from the group of: an ellipse, an oval, a trapezoid, a rounded rectangle, a parallelogram, a pentagon, hexagon, and an octagon.

22. The intraocular lens of claim 1, wherein the first foldable material is the same as the second foldable material.

23. The intraocular lens of claim 1, wherein the first foldable material is different from the second foldable material.

24. The intraocular lens of claim 1, wherein the optical assembly comprises at least one projection extending away from an outer circumferential surface thereof and which is configured to engage the aperture defined in the flange of the base lens.

25. The intraocular lens of claim 1, wherein the optical assembly is a single component.

26. The intraocular lens of claim 25, wherein the single component corrects at least one of sphere cylinder presbyopia, spherical aberrations, and higher order optical aberrations.

* * * * *